United States Patent
Rønfeldt Thomsen et al.

(10) Patent No.: US 10,358,681 B2
(45) Date of Patent: Jul. 23, 2019

(54) MICRORNA-BASED METHOD FOR ASSESSING THE PROGNOSIS OF A PROSTATE CANCER PATIENT

(71) Applicants: Exiqon A/S, Vedbaek (DK); Aarhus Universitet, Århus C (DK); Region Midtjylland, Viborg (DK)

(72) Inventors: Anni Rønfeldt Thomsen, Virum (DK); Helle Kristensen, Aarhus V (DK); Karina Dalsgaard Sørensen, Århus C (DK); Lars Kongsbak, Holte (DK); Peter Mouritzen, Jyllinge (DK); Torben Ørntoft, Silkeborg (DK)

(73) Assignees: Aarhus Universitet, Århus C (DK); Region Midtjylland, Viborg (DK); QIAGEN GmbH, Hilden (DE)

( * ) Notice: Subject to any disclaimer, the term of this patent is extended or adjusted under 35 U.S.C. 154(b) by 0 days.

(21) Appl. No.: 15/554,060

(22) PCT Filed: Feb. 26, 2016

(86) PCT No.: PCT/DK2016/050053
§ 371 (c)(1),
(2) Date: Aug. 28, 2017

(87) PCT Pub. No.: WO2016/134727
PCT Pub. Date: Sep. 1, 2016

(65) Prior Publication Data
US 2018/0044737 A1    Feb. 15, 2018

(30) Foreign Application Priority Data
Feb. 27, 2015 (DK) .......................... PA 2015 00113

(51) Int. Cl.
*A61K 48/00* (2006.01)
*C07H 21/02* (2006.01)
*C07H 21/04* (2006.01)
*C12Q 1/6886* (2018.01)

(52) U.S. Cl.
CPC ...... *C12Q 1/6886* (2013.01); *C12Q 2600/118* (2013.01); *C12Q 2600/158* (2013.01); *C12Q 2600/178* (2013.01)

(58) Field of Classification Search
CPC .......................... C12N 2310/11; C12N 31/713
See application file for complete search history.

(56) References Cited

U.S. PATENT DOCUMENTS

| | | | |
|---|---|---|---|
| 2014/0235469 A1* | 8/2014 | Shelton | C12Q 1/6886 506/9 |
| 2014/0309130 A1 | 10/2014 | Haj-Ahmad | |
| 2018/0002762 A1 | 1/2018 | Chakravarti et al. | |
| 2018/0030542 A1 | 2/2018 | Thomsen et al. | |

FOREIGN PATENT DOCUMENTS

| | | | | |
|---|---|---|---|---|
| CN | 103882118 A | 6/2014 | | |
| EP | 2341145 A1 | 7/2011 | | |
| WO | WO-2009/036236 A1 | 3/2009 | | |
| WO | WO 2011/057003 A2 * | 5/2011 | ......... | C12N 2310/11 |
| WO | WO-2011/127219 A1 | 10/2011 | | |
| WO | WO-2012015765 A2 | 2/2012 | | |
| WO | WO-2013/063544 A1 | 5/2013 | | |
| WO | WO-2014/071205 A1 | 5/2014 | | |
| WO | WO-2014/085906 A1 | 6/2014 | | |
| WO | WO 2016/046365 A1 * | 3/2016 | ......... | C12N 2310/11 |

OTHER PUBLICATIONS

"Arraystar Handbook miRStar(TM) PCR Array Systems," Jul. 3, 2014 http://web.archive.org/web/20150213151200/http://www.arraystar.com/Manage/UploadFile/Handbook/Arraystar%20Handbook-miRStar%20PCR%20Array%20Systems.pdf, retrieved Feb. 13, 2015 (36 pages).
Fu et al., "Deregulated microRNAs in CD4 + T Cells from individuals with latent tuberculosis versus active tuberculosis," J. Cell. Mol. Med. 18(3): 503-513 (2014).
International Search Report and Written Opinion for International Patent Application No. PCT/DK2016/050053, dated Jun. 1, 2016 (11 pages).
Kim et al., "Virus-Encoded microRNAs HSV1-MIR-H18 and HSV2-MIR-H9-5p: Valuable Diagnostic Biomarkers for Prostate Cancer," Urology 84(4): S71, MP-12.03, 2014 (1 page).
Search Report for Danish Patent Application No. PA 2015 00113, dated Oct. 12, 2015 (11 pages).
Song et al., "Expression Profile Analysis of microRNAs in Prostate Cancer by Next-Generation Sequencing," The Prostate 75(5): 500-516 (2015).
Mlcochova et al., "Urine microRNAs as potential noninvasive biomarkers in urologic cancers," Urol Oncol. 32(1):41.e1-9 (2014).

* cited by examiner

*Primary Examiner* — Amy H Bowman
(74) *Attorney, Agent, or Firm* — Clark & Elbing LLP

(57) ABSTRACT

The present application concerns a new in vitro method for assessing the prognosis of a prostate cancer patient, comprising measuring the expression level of at least two miRs selected from group of miRs consisting of: miR-106a-5p, miR-10b-5p, miR-133a-3p, mi R-152-3p, miR-185-5p, miR-193a-5p, miR-221-3p, miR-23a-3p, miR-30d-3p, miR-326, mi R-374b-5p, miR-615-3p and mi R-625-3p in a RNA sample from prostate cells obtained from said patient, wherein a changed expression level of said at least 2 miRs, as compared to a reference expression profile, is indicative of the prognosis of said prostate cancer patient.

14 Claims, 5 Drawing Sheets

Figure 1:
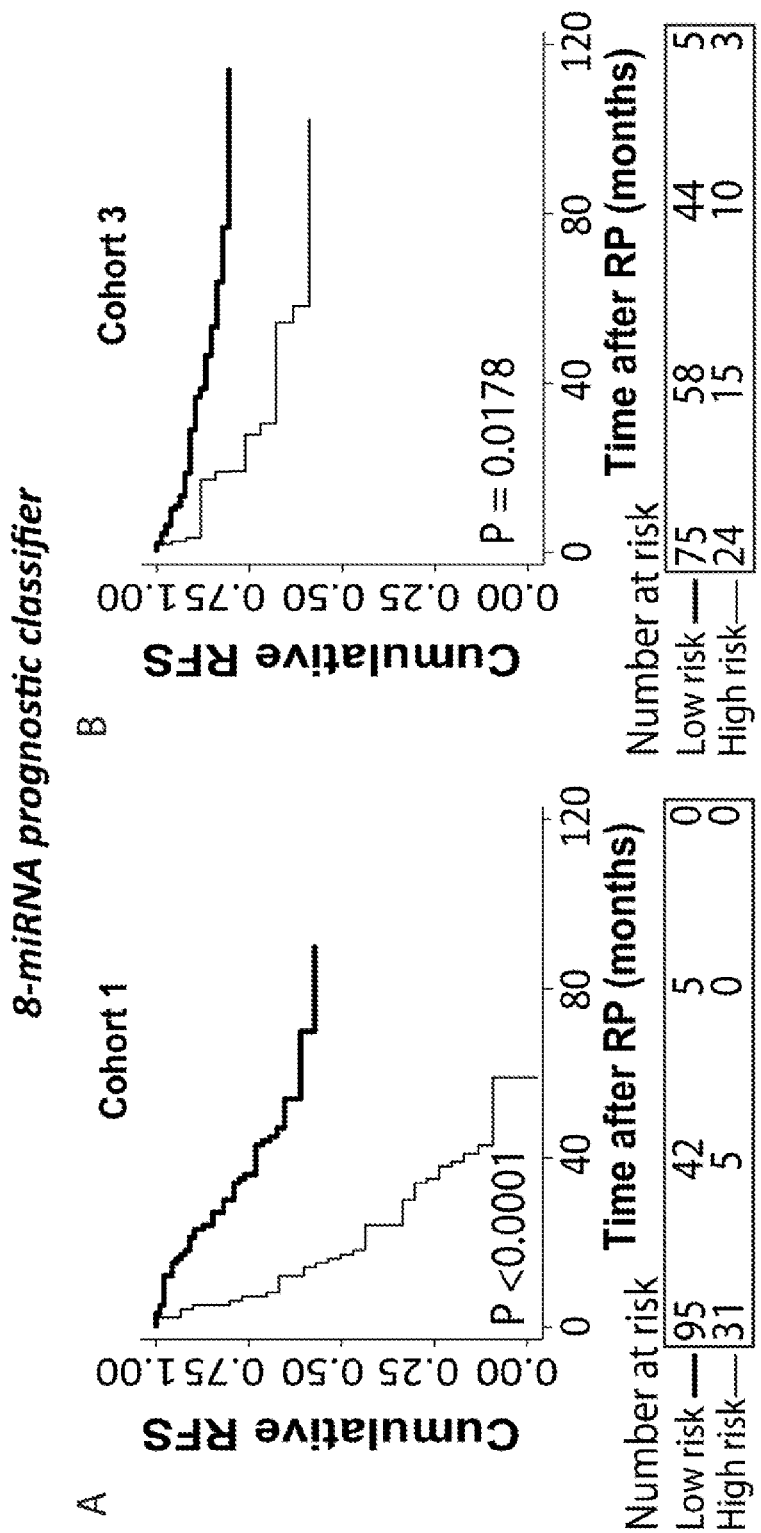

Specification includes a Sequence Listing.

MICRORNA-BASED METHOD FOR ASSESSING THE PROGNOSIS OF A PROSTATE CANCER PATIENT

FIELD OF THE INVENTION

The present invention relates to prediction of prostate cancer aggressiveness (prognosis) at the time of diagnosis (or later) by measuring the level of a few characteristic microRNA biomarkers in prostate tissue, in order to guide treatment decisions (e.g. active surveillance, surgery, radiation).

BACKGROUND OF THE INVENTION

Prostate cancer is the most frequently diagnosed male cancer and the fifth leading cause of cancer-associated mortality in Western countries (1). Prostate cancer is typically diagnosed on the basis of increased serum prostate specific antigen (PSA) levels followed by histopathological inspection of needle biopsies.

The use of PSA for prostate cancer detection, however, is associated with considerable false positive rates and does not distinguish well between indolent and aggressive tumors. During the past decades, increased use of PSA testing and PSA based screening has resulted in higher incidences as well as down-staging of the disease.

However, PSA as well as the other currently available prognostic indicators (mainly number of positive biopsies, clinical TNM stage and Gleason score) are unable to accurately predict patients with an aggressive prostate cancer that requires instant treatment. This leads to marked overtreatment, and many patients undergo unnecessary RP or radiation therapy, which is associated with side effects worse than living with the untreated non-lethal prostate cancer.

Hence, there is a serious unmet need in prostate cancer diagnostics to develop methods which can improve the prognostic assessment by correctly distinguishing between non-aggressive cancers, that safely can be managed by active surveillance, and aggressive cancers that will benefit from early intervention.

An emerging new class of potential biomarkers for prostate cancer is the microRNA.

MicroRNAs comprise a class of endogenous small non-coding regulatory RNAs (~22 nt), which control gene expression at the posttranscriptional level in diverse organisms, including mammals (2). MicroRNAs are transcribed as long imperfect paired stem-loop primary microRNA transcripts (pri-microRNAs) by RNA polymerase II, and further processed into hairpin precursor microRNAs (pre-microRNAs) by the nuclear RNase III endonuclease, Drosha (3). After export to the cytoplasm by Exportin-5-Ran-GTP, another RNase III endonuclease, Dicer, cleaves the pre-microRNA into a mature ~22 nt microRNA duplex (3). Mature microRNAs mediate their function while incorporated in the microRNA-induced silencing complex (miRISC). The microRNA guides this complex to perfect/near perfect complementary target mRNAs, leading to either translational inhibition or mRNA degradation (4).

MicroRNAs are one of the most abundant classes of gene regulatory molecules and the latest release of the miRBase (version 21) contains 2588 mature human microRNAs (1881 precursors) http://www.mirbase.org/ (5). Together microRNAs have been estimated to regulate up to two thirds of all human mRNAs. Consequently, microRNAs influence numerous processes in the cell, for instance cell differentiation, cell cycle progression and apoptosis, and deregulation of microRNAs are often connected to human pathologies, including cancer (6). Additionally, some microRNAs appear to be cell type and disease specific and deregulated microRNA expression has been associated with both development and progression of cancer (7). Thus, aberrant microRNA expression has been investigated as a promising potential source of novel biomarkers for early cancer diagnosis (7). Moreover, microRNAs have potential to be used as targets of microRNA-based therapeutics for cancer (8). Several microRNA profiling studies have also reported aberrantly expressed microRNAs in the development and/or progression of prostate cancer (9). However, most of the microRNA biomarker studies in prostate cancer published to date have used relatively low patient sample numbers and often lack stringent independent clinical validation to confirm the biomarker potential of the identified microRNA candidates.

Importantly, to the best of our knowledge, no prognostic method based on microRNA biomarkers able to predict the risk of prostate cancer recurrence has been discovered.

Here we performed miRnome profiling of more than 750 of the most abundant microRNAs and identified the significantly aberrant regulated microRNAs in prostate tumor tissue FFPE samples from patients with vs. without biochemical recurrence (BCR) after radical prostatectomy (RP). We identified five prognostic classifiers in cohort 1 and evaluated their prognostic accuracy as predictors of time to recurrence—monitored as biochemical recurrence (PSA) after removal of the prostate (radical prostatectomy (RP)) (Example 1). The prognostic accuracy of the classifiers was then validated in two independent radical prostatectomy cohorts (cohort 2 and cohort 3) (Example 2-6). Despite the fact that prostate tumor samples in cohort 3 were of different national origin (U.S.), sampled in a different manner (snap-frozen), subjected to different RNA extraction procedures, analyzed by a different microRNA expression detection platform, and different Cohort characteristics (Cohort 3 was generally less aggressive and had fewer events of recurrence than cohort 1 and 2), four of our microRNA prognostic classifier performed equally well on the external cohort, underlining the robustness of these classifiers.

The five prognostic microRNA classifiers all showed significant independent prognostic value for prediction of time to BCR after RP, beyond routine clinicopathological variables.

SUMMARY OF THE INVENTION

As the prostate specific antigen (PSA) method is associated with considerable false negative rates and does not distinguish well between clinically indolent or aggressive tumors, there is a need for novel markers of prostate cancer that can be used on their own or in combination with existing markers. The present invention present one set of markers and a method to apply them for assessment of prognosis (tumor aggressiveness/risk of recurrence).

In first aspect, the invention thus concerns an in vitro method for prediction of prostate cancer prognosis, comprising measuring the expression level of at least two miRs selected from a group of 13 miRs consisting of: miR-106a-5p, miR-10b-5p, miR-133a-3p, miR-152-3p, miR-185-5p, miR-193a-5p, miR-221-3p, miR-23a-3p, miR-30d-3p, miR-326, miR-374b-5p, miR-615-3p and miR-625-3p, in a RNA sample of cells from a biopsy taken from a prostate cancer patient, wherein a changed expression level of said at least 2 miRs, as compared to a reference expression profile, is indicative of the prognosis of said patient.

A second aspect of the invention relates to a kit for in vitro assessment of prostate cancer prognosis.

A third aspect of the invention relates to a method of treating a patient in need of prostate cancer treatment, the method comprise performing the in vitro method of first aspect, characterizing the patients with respect to their prognosis, and selecting an appropriate therapy for the patient based on this information. Obviously, the prognosis is a crucial factor to consider when the further treatment of the patient is planned, since a very bad prognostic evaluation would disfavour stressful and agonizing procedures.

Definitions

Harrell's concordance index, or c-index, refer to a generalized area under the receiver operating curve (AUC) for censored observations and is equal to the probability of concordance between the predicted probability of relapse and the relapse outcome (Harrell (2001) Regression modelling strategies: with applications to linear models, logistic regression, and survival analysis. New York: Springer-Verlag).

The expression "microRNA", "miRNA" and "miR" are used synonymously to refer to an about 18-25 nucleotide (nt) long, non-coding RNAs derived from endogenous genes. MicroRNAs are processed from longer (ca 75 nt) hairpin-like precursors termed pre-miRs. MicroRNAs assemble in complexes termed miRISCs and recognize their targets by antisense complementarity. If the microRNAs match 100% their target, i.e. the complementarity is complete, the target mRNA is cleaved, and the miR acts like a siRNA. If the match is incomplete, i.e. the complementarity is partial, then the translation of the target mRNA is blocked.

The term "expression", as used herein, refers to the transcription and/or accumulation of RNA-molecules within a cell or a tissue sample.

In the present context the terms "expression level of a miR", "miR expression level" and "level of a miR" are used synonymously as a measure of the "amount of a specific miR" that is detected in the sample. The "amount of a specific miR" may be expressed in either absolute, relative or normalized measures and refers to values obtained by both quantitative, as well as qualitative methods. One particularly preferred measure of the "amount of a specific miR" is the Crossing point (Cp) value obtained by qRT-PCR as described below and in the examples, but "amount" may as well be quantified by digital PCR, or various Next Generation Sequencing methods. In certain situations, e.g. when ratios of miR expression levels are used to calculate a prognostic score, the absolute determined expression levels of the miRs suffice. However, as an alternative to making determinations based on the absolute expression level of the miRs, determinations may be based on the normalized expression levels of the miRs.

Expression levels are normalized by correcting the absolute expression level of a miR by comparing its expression to the expression of a gene that is constitutively or nearly constitutively expressed. Suitable genes often used for normalisation include housekeeping genes such as the actin gene. In the present study we use miR-151a-5p for normalization.

As used herein the terms: miR-106a-5p, miR-10b-5p, miR-133a-3p, miR-152-3p, miR-185-5p, miR-193a-5p, miR-221-3p, miR-23a-3p, miR-30d-3p, miR-326, miR-374b-5p, miR-615-3p, miR-625-3p and miR-151a-5p refer to the human miR sequences found in miRNA registry database release 12.0 or later and hosted by Sanger Institute, UK as well as their animal equivalents. See also table 9.

The term "prognosis" is herein defined to encompass the following processes either individually or cumulatively depending upon the clinical context: forecasting as to the probable outcome of a disease state or determining the prospect as to recovery from a disease as indicated by the nature and symptoms of a case.

In the present context "reference expression profile" designate the expression level of two or more miRs selected from a group of 13 miRs consisting of: miR-106a-5p, miR-10b-5p, miR-133a-3p, miR-152-3p, miR-185-5p, miR-193a-5p, miR-221-3p, miR-23a-3p, miR-30d-3p, miR-326, miR-374b-5p, miR-615-3p and miR-625-3p in samples of cells obtained from prostate cancer patients whose cancer did not progressed significantly within a period of 5 years after the sampling.

The term "robustness" in connection with miR classifier is used herein to describe a classifier which provide relative similar outcome with respect to the assessment of the prognosis of a prostate cancer patient even though somewhat different sampling and quantitation methodologies are used.

"UniRT" is a qRT-PCR method marketed by Exiqon A/S. The method and its performance is described in Example 1 and 7 and in Danish Patent Application PA 2009 00156, EP2391736 and Mestdagh et al. Nat Methods. 2014 August; 11(8):809-15.

Embodiments of the present invention are described below, by way of examples only.

DETAILED DISCLOSURE OF THE INVENTION

The technical problem underlying the invention is the provision of an alternative in vitro method for assessing the prognosis of a prostate cancer patient. In particularly a method which may supplement, or perhaps even substitute, other currently available prognostic indicators (mainly the PSA test, the number of positive biopsies, the clinical TNM stage and the Gleason score).

In Example 1, we describe the application of two different statistical approaches (1. a leave one out cross validation (LOOCV) and 2. Combinations of microRNAs significant in univariate Cox regression analysis) to arrive at five prognostic miR-classifiers, see table 1, 2 and 3. Collectively the two approaches provided classifiers, when combined, consisting of 13 miRs, namely: miR-106a-5p, miR-10b-5p, miR-133a-3p, miR-152-3p, miR-185-5p, miR-193a-5p, miR-221-3p, miR-23a-3p, miR-30d-3p, miR-326, miR-374b-5p, miR-815-3p and miR-625-3p (Table 3).

Figure 5:
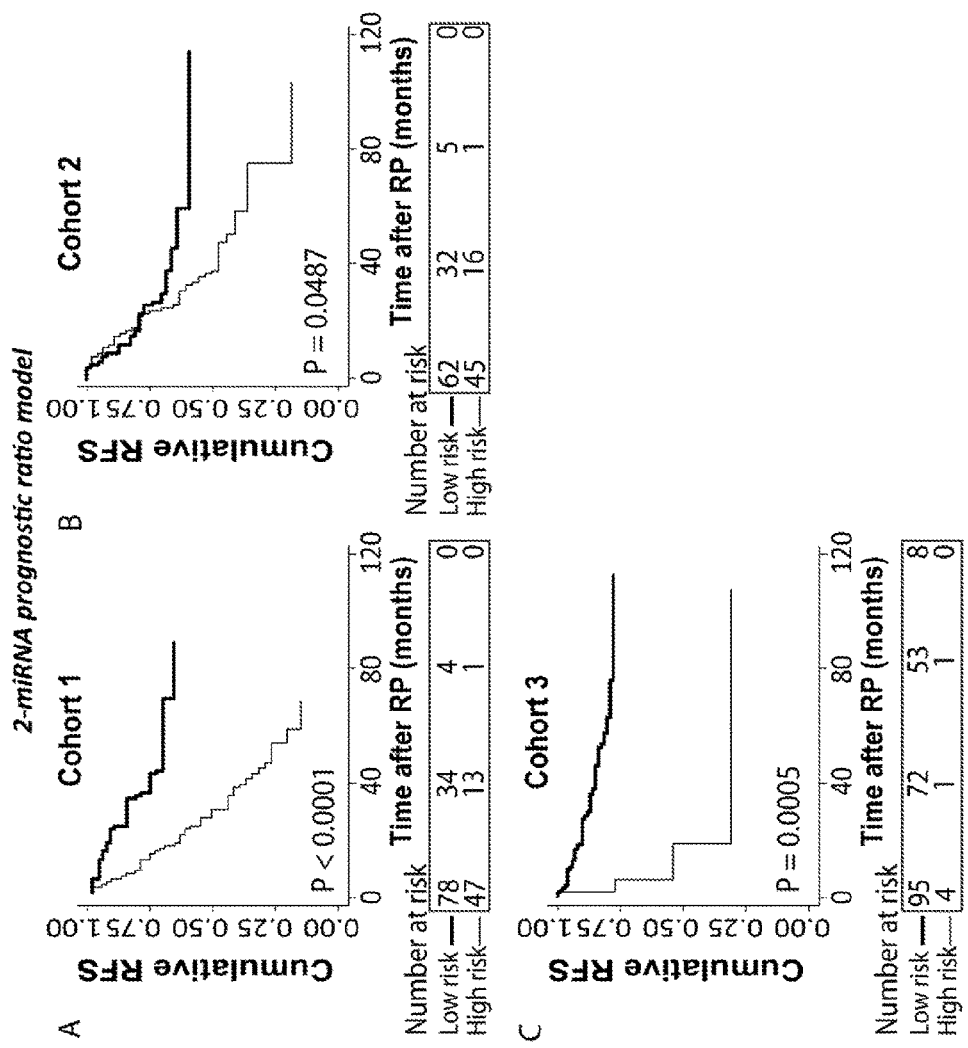

Surprisingly, we have found that as few as 2 miRs drawn from this group of 13 miRs can be used to differentiate between recurrent vs. non-recurrent cases, and predict time to biochemical recurrence after radical prostatectomy (BCR; see Example 1+6, FIG. 5 and table 8). Accordingly, one aspect of the present invention is an in vitro method for assessing the prognosis of a prostate cancer patient, comprising measuring the expression level of at least two miRs selected from group of miRs consisting of: miR-106a-5p, miR-10b-5p, miR-133a-3p, miR-152-3p, miR-185-5p, miR-193a-5p, miR-221-3p, miR-23a-3p, miR-30d-3p, miR-326, miR-374b-5p, miR-615-3p and miR-625-3p in RNA from a prostate tissue sample obtained from a said patient, wherein a changed expression level of said at least 2 miRs, as compared to a reference expression profile, is indicative of the prognosis of said patient.

The 8 miRNAs with highest impact on the prognostic accuracy from the discovery and validation study using the leave-one-out cross-validation (LOOCV) maximum likelihood classification procedure (see Example 1) appears attractive. Thus one embodiment of the present invention is an in vitro method for assessing the prognosis of a prostate cancer patient (i.e. the risk that a subject harbors aggressive prostate cancer) comprising measuring the expression level of at least two miRs selected from group of miRs consisting of: miR-106a-5p, miR-152-3p, miR-185-5p, miR-193a-5p, miR-221-3p, miR-23a-3p, miR-374b-5p and miR-615-3p in a sample of cells obtained from said patient, wherein a changed expression level of said at least 2 miRs, as compared to a reference expression profile, indicates a less favorable prognosis.

In order to serve the requirements of every day clinics, a prognostic method must provide relative similar outcome with respect to differentiating between patients with a good or a bad prognosis even though somewhat different sampling and quantitation methodologies are used. The method should be robust. Encouragingly, despite the fact that tumor samples in cohort 3 were of different national origin (U.S.), sampled in a different manner (snap-frozen), subjected to different RNA extraction procedures and analysed by a different microRNA expression detection platform (Agilent Human miRNA Microarray 2.0, and different cohort characteristics (cohort 3 was generally less aggressive, and had fewer events of recurrence than cohort 1), our 8-microRNA prognostic classifier performed equally well on this cohort, underlining the robustness of the 8-microRNA prognostic classifier, see example 2 and table 4.

Measuring 13 or even 8 miRNAs may appear as impractically for a prognostic tests intended for everyday clinics. In Example 1+3-6, table 5-8, a number of reduced miRNA classifiers with prognostic value drawn from this list of 13 miRNAs (Table 3) are shown.

Surprisingly, these reduced miRNA classifiers appear even more robust than the 8-microRNA prognostic classifier. Accordingly, other aspects of the present invention are in vitro methods for assessing the prognosis of a prostate cancer patient, comprising measuring the expression level of: miR10b-5p, miR-133a-3p, miR-23a-3p and miR-374b-5p; or the level of: miR-185-5p, miR-221-3p and miR-326; or the level of: miR-152-3p, miR-185-5p and miR-221-3p; or even the level of only: miR-10b-5p and miR-374b-5p in a sample of cells obtained from said patient, wherein a changed expression level of said at least 2 miRs, as compared to a reference expression profile, is indicative of the prognosis of said patient.

The "amount of a specific miR" may be expressed in either absolute, relative or normalized measures and refers to values obtained by both quantitative, as well as qualitative methods.

As an alternative to making determinations based on the absolute expression level of the miRs, determinations may be based on the normalized expression levels of the miRs. Expression levels are normalized by correcting the absolute expression level of a miR by comparing its expression to the expression of a gene that is constitutively or nearly constitutively expressed. Housekeeping genes such as the actin gene are often used for normalization. However, in the case of short RNAs such as miRs certain invariable miRNAs are preferred as normalizers.

Accordingly, in one embodiment of the invention the expression levels are normalized expression levels. In the present study we use miRs for normalizing. Using the NormFinder algorithm (10), we identified miR-151a-5p as the most stably expressed miRNA in the discovery study. Comparison of two normalization strategies (global mean and miR-151-5p) gave very similar results in terms of top differentially expressed miRNAs as well as in the overall ranking of miRNAs. Therefore in one embodiment of the invention expression levels are normalized to the expression level of miR-151a-5p.

When applying a prognostic assay in practice it is advantageous to use the assay values to calculate a prognostic score (P) allowing one to define cut-off values and to assess the prognosis of a prostate cancer patient based on the prognostic score. Thus one embodiment of the present invention is a method, wherein the assessment of the cancer patients prognosis involves detecting the level of said at least two miRs in a said sample and calculate a prognostic score (P) based on a dataset comprising the expression level data of at least two miRs.

The level of miRs may conveniently be quantified by quantitative real-time Reverse Transcriptase mediated Polymerase Chain Reaction method, qRT-PCR (17). Thus in one embodiment of the invention the expression level of said miRs is determined by the method of RT-QPCR, RT-qPCR or qRT-PCR, which are synonymous.

One particularly preferred measure of the "amount of a specific miR" is the Crossing point (Cp) value obtained by qRT-PCR. Another preferred measure of the "amount of a specific miR" is the "threshold cycle value (Ct)" value likewise obtained by qRT-PCR as described in the examples. The Cp and the Ct measures of the "amount of a specific miR" provide roughly similar measures, see (12). Whether to choose Cp or Ct is largely a matter of choice of the machine the assay tied to and performed on. If the amplification is performed in a LightCycler® 480 Real-Time PCR System using the Roche LC software the amount of a specific miR is expressed by the Cp. If the amplification is performed in Applied Biosystems ABI Prism 7900HT 384-well instrument using the software provided with it the amount of a specific miR is expressed by the Ct. The following refer to the Cp-value but apply as well to the Ct-value and to the "quantification cycle" (Cq) value.

The Cp-value is related to the level of e.g. a specific miR, by the relation:

$$\text{(liniar) expression level of } miRx \sim 2^{-Cp(normalised\ miRx)}$$

Wherein Cp(miRx) designates the Cp-readout from real-time qRT-PCR instrument specifically detecting one specific miR called miRx. Example 1 describes such an assay in details.

Ratio based markers offers an attractive classifier model due to its independence of data normalization. We found that a ratio classifier drown from the 13 miRs (or the 11 miRs from the "Cox Regression") could be used as independent prognostic biomarkers for prediction of time to prostate cancer recurrence, see example 5.

Accordingly, when the Cp-values are used as quantifiers of miR-levels, e.g. the expression:

$$\frac{(\text{level of } miR23a-3p) \times (\text{level of } miR10b-5p)}{(\text{level of } miR133a-3p) \times (\text{level of } miR374b-5p)}$$

is equivalent to:

$$Cp(miR23a\text{-}3p)+Cp(miR10b\text{-}5p)-Cp(miR133a\text{-}3p)-Cp(miR374b\text{-}5p)$$

Accordingly, in one embodiment of the invention the diagnostic prognostic score (P)—for the 4-miR classifier (miR10b-5p, miR-133a-3p, miR-23a-3p and miR-374b-5p) is calculated as:

$$P = X \times C(miR23a\text{-}3p) + Y \times C(miR10b\text{-}5p) + Z \times C(miR133a\text{-}3p) + W \times C(miR374b\text{-}5p)$$

where the coefficients X, Y, Z and W are determined by the regression-analysis according to the particular set-up, and C is the threshold cycle value (Ct), or the crossing point value (Cp), or the "quantification cycle" (Cq) value, or any value similar to those.

Surprisingly, we have found that a ratio based classifier consisting of only two of the four miRNAs drawn from the group of 13 miRs could be used as independent prognostic biomarkers for prediction of prostate cancer recurrence, see Example 6.

Accordingly one further embodiment of the present invention is an in vitro method for assessing the prognosis of a prostate cancer patient, comprising measuring the expression level of the two miRs: miR-374b-5p and miR-10b-5p.

When the miRs are quantified by qRT-PCR and Cp-values are used as quantifiers of miR-levels, the expression:

$$\frac{(\text{level of } miR10b-5p)}{(\text{level of } miR374b-5p)}$$

is equivalent to:

$$Cp(miR10b\text{-}5p) - Cp(miR374b\text{-}5p)$$

Similarly, in one embodiment of the invention the diagnostic prognostic score (P)—for the 2-miR classifier is $$P = X \times Cp(miR10b\text{-}5p) + Y \times Cp(miR374b\text{-}5p)$$

where the coefficients X and Y are determined by the regression-analysis, and C is the threshold cycle value (Ct), or the crossing point value (Cp), or the "quantification cycle" (Cq) value, or any value similar to those.

Both linear and other types of regression are contemplated.

By "machine learning" is referred to a process which takes advantage of computer algorithms that improve automatically through experience, in the art this process of improving the algorithms is often referred to as "training". Machine learning can be used to discover general rules in large data sets, machine learning can e.g. be used to extract clinical informative data from a dataset comprising miR expression in cancer and non-cancer samples of the prostate. A general treatise of the concept of machine learning can be found in (Tom Mitchell, Machine Learning, McGraw Hill, 1997). Accordingly in one embodiment of the invention the algorithm for calculating the diagnostic prognostic score (P) was reached applying machine learning.

While the Quantitative real-time Reverse Transcriptase mediated Polymerase Chain Reaction method, qRT-PCR is the preferred method of quantitating. Example 2, 3, 4 and 6 show that the invention is compatible with microarray based quantitation and accordingly one embodiment of the invention is a method wherein the expression levels of said miRs are measured by microarray.

Other methods of quantitation such as Northern blots, quantitative digital PCR and various quantitative Next Generation Sequencing methods are contemplated, and thus embodiments of the invention.

A further aspect of the invention is a kit for in vitro assessment of the prognosis of a prostate cancer patient, comprising measuring the expression level of at least two miRs selected from group of 13 miRs consisting of: miR-106a-5p, miR-10b-5p, miR-133a-3p, miR-152-3p, miR-185-5p, miR-193a-5p, miR-221-3p, miR-23a-3p, miR-30d-3p, miR-326, miR-374b-5p, miR-615-3p and miR-625-3p in a RNA sample from prostate cells obtained from said patient, wherein a changed expression level of said at least 2 miRs, as compared to a Reference Expression Profile, is indicative of the prognosis of said patient.

25 The invention is further illustrated in the following non-limiting examples, tables and figures.

LEGENDS

FIG. 1. Kaplan-Meier survival analysis of recurrence free survival (RFS) based on the 8-miRNA prognostic classifier (table 4) in radical prostatectomy (RP) samples from two independent cohorts. Patients in the training cohort 1 (A) were divided into low vs. high risk groups after ROC analysis. Patients in validation cohort 3 (B) were divided into low/high risk groups according to the cut-off (fraction) defined in cohort 1. Significant p-values for two-sided log-rank test are given. High molecular risk status, as defined by the 8-miRNA prognostic classifier, was significantly associated with early biochemical recurrence after RP.

Figure 2:
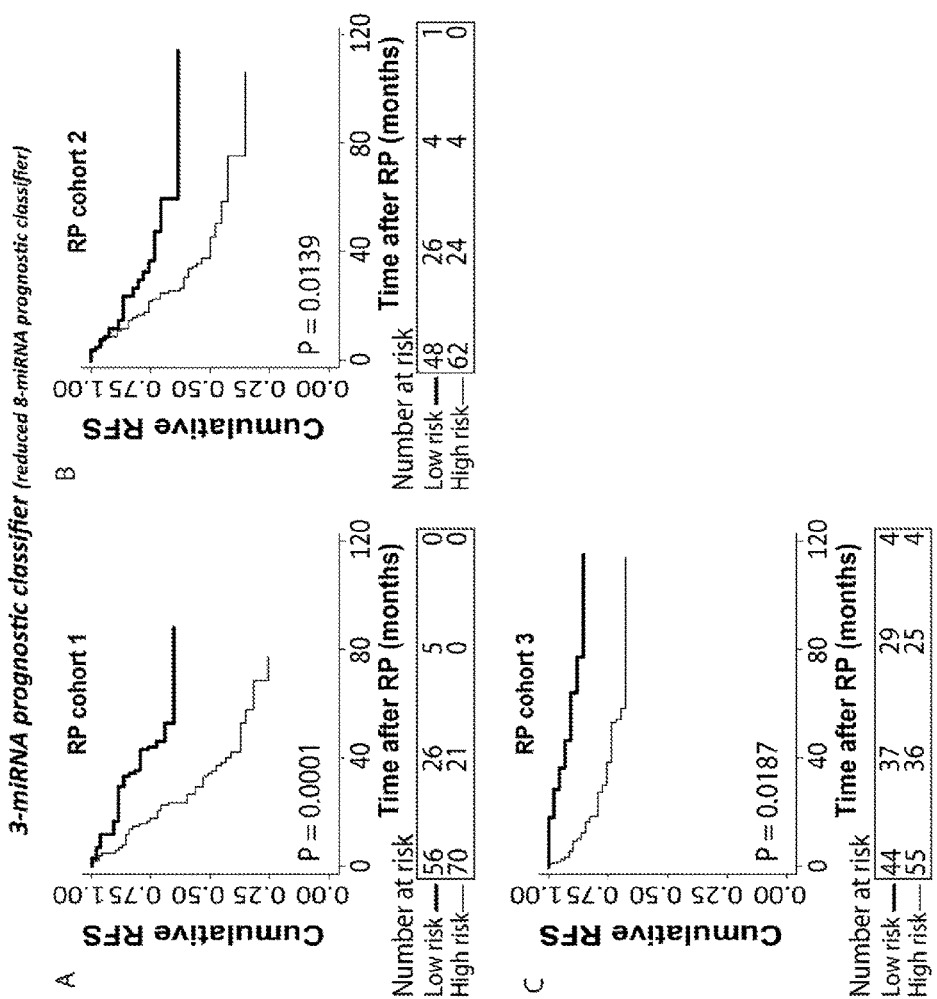

FIG. 2. Kaplan-Meier survival analysis of recurrence free survival (RFS) based on the reduced 8-miRNA prognostic classifier (miR-185-5p+miR-221-3p+miR-152-3p, table 5) in radical prostatectomy (RP) samples from three independent cohorts. Patients in the training cohort 1 (A) were divided into low vs. high risk groups after ROC analysis. Patients in validation cohort 2 (B) were divided into low/high risk groups according to the cut-off (fraction) defined in cohort 1. This was done in the same way for the external validation cohort 3 (Taylor et al. And Hieronymus et al; B). Significant p-values for two-sided log-rank test are given. High molecular risk status, as defined by the reduced 8-miRNA prognostic classifier was significantly associated with early biochemical recurrence after RP in three independent cohorts.

Figure 3:
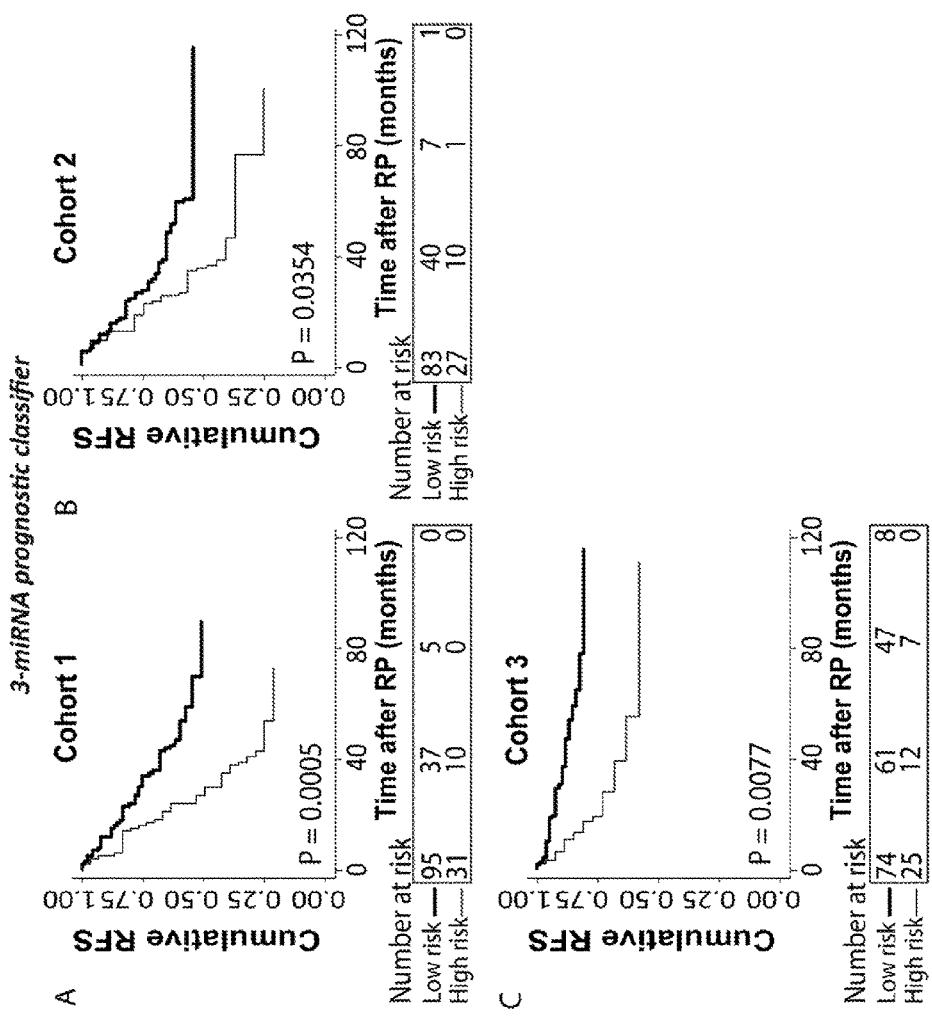

FIG. 3. Kaplan-Meier survival analysis of recurrence free survival (RFS) based on the 3-miRNA prognostic classifier (miR-185-5p+miR-221-3p+miR-326, table 6) in radical prostatectomy (RP) samples from three independent cohorts. Patients in the training cohort 1 (A) were divided into low vs. high risk groups after ROC analysis. Patients in validation cohort 2 (B) were divided into low/high risk groups according to the cut-off (fraction) defined in cohort 1. This was done in the same way for the external validation cohort 3 (Taylor et al And Hieronymus et al.; C). Significant p-values for two-sided log-rank test are given. High molecular risk status, as defined by the 3-miRNA prognostic classifier, was significantly associated with early biochemical recurrence after RP in three independent cohorts.

Figure 4:
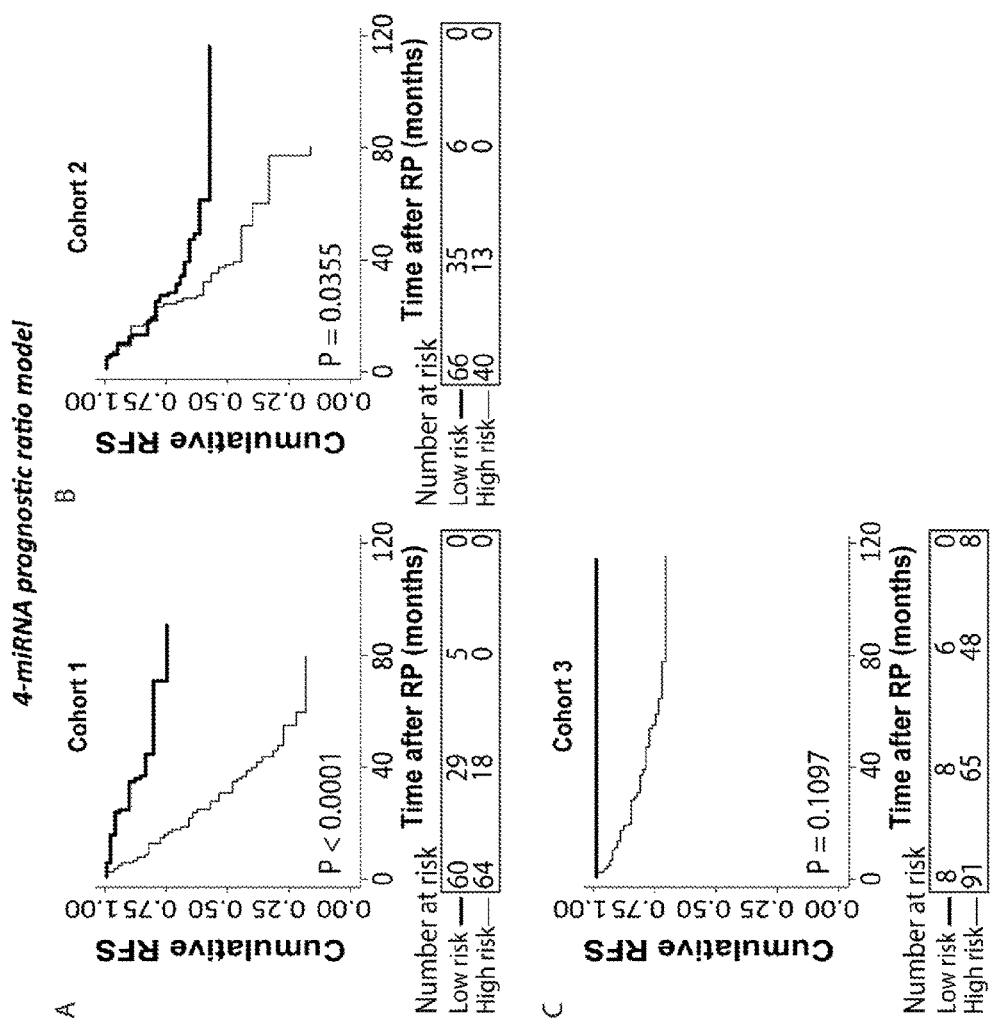

FIG. 4. Kaplan-Meier survival analysis of recurrence free survival (RFS) based on the 4-miRNA prognostic ratio model (miR-10b-5p×miR-23a-3p/miR-133a-3p×miR-374b-5p ratio, table 7) in radical prostatectomy (RP) samples from three independent cohorts. Patients in the training cohort 1 (A) were divided into low vs. high risk groups after ROC analysis. Patients in validation cohort 2 (B) were divided into low/high risk groups according to the absolute cut-off value defined in cohort 1. This was done in the same way for the external validation cohort 3 (Taylor et al. And Hieronymus et al, C). P-values for two-sided log-rank test are given. High molecular risk status, as defined by the 4-miRNA prognostic ratio model, was significantly associated with early biochemical recurrence after RP.

FIG. 5. Kaplan-Meier survival analysis of recurrence free survival (RFS) based on the 2-miRNA prognostic ratio model (miR-10b-5p/miR-374b-5p, table 8) in radical prostatectomy (RP) samples from three independent cohorts. Patients in the training cohort 1 (A) were divided into low vs. high risk groups after ROC analysis. Patients in validation cohort 2 (B) were divided into low/high risk groups according to the absolute cut-off value defined in cohort 1. This was done in the same way for the external validation cohort 3 (Taylor et al., And Hieronymus et al., C). P-values for two-sided log-rank test are given. High molecular risk status, as defined by the 2-miRNA prognostic ratio model, was significantly associated with early biochemical recurrence after RP in three independent cohorts.

EXAMPLE 1

Novel Prognostic Classifiers for Prediction of Prostate Cancer Recurrence Identified by Genome-Wide microRNA Profiling.

Aim of Study

To investigate prognostic biomarker potential of microRNA expression in prostate cancer and build a classifier for risk stratification.

Methods

Specimens

All samples were collected at Department of Urology and obtained from Institute of Pathology, Aarhus University Hospital, Denmark (from 1997-2005). The training cohort (cohort 1) consisted of 127 curatively intended RPs of histologically verified clinically localized prostate cancer. All tissue specimens were evaluated by a trained pathologist. Representative regions with >90% tumor were marked on hematoxylin and eosin (H&E) stained sections, and punch biopsies were taken from the corresponding FFPE blocks for RNA extraction as described in (Haldrup 2013). Total RNA was isolated from 1.5 mm punch biopsies using the miRNeasy FFPE Kit (Qiagen), according to the manufacturer's instructions. The 260/280 nm absorbance ratio (optimal ratio: 2.0) was used as quality assurance for the RNA samples. RNA samples with a ratio<1.75 were excluded from further analysis. The purified RNA was stored at −80° C.

MicroRNA Expression Profiling

MicroRNA expression profiling (all reagents from Exiqon) was performed at Exiqon A/S, Vedbaek, Denmark, using the miRCURY LNA™ Universal RT microRNA PCR platform. In brief, 40 ng total RNA was reverse transcribed in 40 µl reactions using the miRCURY LNA™ microRNA PCR, Polyadenylation and cDNA synthesis kit II. cDNA was diluted 100× and analyzed in 10 µl PCR reactions. For cohort 1 (training), relative expression levels of 752 miRNAs were analyzed using microRNA Ready-to-Use PCR, Human panel I+II, V3R, in 384-well PCR plates. Negative controls (no template in reverse transcription reaction) were run in parallel. Amplification was performed using the LightCycler® 480 Real-Time PCR System (Roche) and ExiLENT SYBR® Green master mix. Amplification curves were analyzed using the Roche LC software for determination of quantification cycle (Cq) values (by the 2nd derivative method (Livak, 2001) and for melting curve analyses. MicroRNAs detected with <3 Cq less than the negative control or for which all Cq values exceeded 37 in all samples were excluded from further analyses (cohort 1: 97 miRNAs, cohort 2: no miRNAs).

For cohort 1 (training), data was normalized to the global mean (i.e. mean for all miRNAs detected in all samples; here n=61, see table 10), previously reported as the best normalization method for qRT-PCR data involving numerous assays (15). By using NormFinder algorithm (10) we found that miR-151a-5p was an optimally stable single normalization gene in cohort 1. The two normalization strategies (miR-151a-5p and global mean normalization) gave very similar results in terms of top differentially expressed microRNAs as well as in the overall ranking of microRNAs in cohort 1, thus supporting the validity of miR-151a-5p as a normalization gene in a subsequent validation study with fewer miRNAs tested. Normalization was done according to the formula $\Delta Cq = Cq_{Normalisation\ factor} - Cq_{miRNA}$. Differences in expression levels are calculated as $\Delta\Delta Cq = \Delta Cq_{group\ 1} - \Delta Cq_{group\ 2}$. To convert this to fold change, the formula $2^{-\Delta\Delta Cq}$ is used. The reciprocal number, multiplied by a factor of −1, was used for downregulated miRNAs.

Statistical Analyses

Unless stated otherwise, statistical analyses were conducted in STATA version 11 (StataCorp, Texas, USA). For all analyses P values <0.05 were considered statistically significant.

Expression Analysis:

The Shapiro Wilk test was used to evaluate if data was normally distributed. As several of the microRNAs were not, a non-parametric statistic Wilcoxon signed-rank test were used for the pairwise comparisons of microRNA expression between the different groups. P values were corrected for multiple testing using the Benjamini-Hochberg method (11).

Classifier Construction:

Leave-one-out cross-validation (LOOCV) maximum likelihood classification procedures were trained and tested in 'R' Bioconductor software version 3.0.0 (Bell Laboratories, Lucent Technologies, http://www.cran.r-project.org/) as previously described (13). Normalized microRNA expression values from 127 (70 without and 57 with biochemical recurrence) RP samples were used for generating a prognostic multi-microRNA classifier constructed to classify prostate cancer recurrence. Only microRNAs expressed in at least 70% of the samples (n=236 miRNAs) were included in the analysis. The performance of the classifiers was tested using a $\chi^2$ test, and calculations of sensitivity and specificity (Table 1). To generate a unified model comprising the 8 miRNAs in the 8-microRNA prognostic classifier (described later) for RFS analyses, each miRNA was weighed by the estimated regression coefficients in the multivariate proportional hazards model, and a combined weighted sum for the miRNA classifier was calculated.

Moreover, we used two different approaches to train prognostic miRNA classifiers from the 11 miRNAs significant in univariate Cox regression analysis in the training cohort (n=126; one of the 127 RP patients was excluded in the RFS analyses due to postoperative endocrine treatment; Table 2). In one approach, each miRNA included in the said classifiers was weighed by the estimated regression coefficients in the multivariate Cox proportional hazards model, and a combined weighted sum for the miRNA classifier was calculated. In the second approach, ratio-based miRNA classifiers were generated based on raw Cq values for each miRNA included in the model.

Prognostic Value:

For recurrence-free survival (RFS) analyses, biochemical recurrence (BCR; PSA cut-off ≥0.2 ng/ml, based on local clinical practice) was used as endpoint. Patients not having experienced BCR were censored at their last normal PSA measurement. The prognostic value of microRNA expression and the weighted sum of microRNA-based classifiers were evaluated by Kaplan-Meier analysis and two-sided log-rank test, and by univariate and multivariate Cox regression analyses as continuous as well as dichotomous variables. For analysis of microRNA expression and the microRNA-based classifiers as dichotomous variables, patients in cohort 1 were divided into high and low expression groups using a cut-off value determined after ROC analysis of no recurrence/recurrence status. All clinicopathological parameters significant in univariate analysis were included in multivariate analyses. Variables failing multivariate analysis were excluded from the final multivariate model through stepwise backward selection. The proportional hazards assumption was verified by the log-negative-log survival distribution function for all variables. The prognostic accuracy of microRNAs and classifiers is evaluated using the Harrell's Concordance Index (C-index); defined as the proportion of all patient pairs in which the predictions and outcomes are concordant, established by univariate and multivariate cox regression analysis.

Results

To investigate the prognostic potential of microRNA expression in prostate cancer, we initially performed biochemical recurrence-free survival (RFS) analysis for 45 candidate miRNAs that were found to be significantly deregulated in the pairwise comparison of pT2 vs. pT3-4, low vs. high Gleason score, and/or recurrent vs. non-recurrent tumors in cohort 1 (data not shown). By univariate Cox regression analysis, 11 of these miRNAs were significantly associated with RFS time in cohort 1 (n=126) (Table 2). More specifically, high expression of miR-10b-5p, miR-23a-3p, miR-185-5p, miR-615-3p, and miR-625-3p and low expression of miR-30d-3p, miR-133a-3p, miR-193a-5p, miR-221-3p, miR-326, and miR-374b-5p was associated with early biochemical recurrence (BCR) in this cohort. However, none of these 11 miRNAs remained significant in a multivariate model including routine clinicopathological factors (PSA, pT stage, Gleason score, and margin status; data not shown) and their prognostic value in univariate analysis in cohort 1 could generally not be confirmed in the independent cohort 2 and cohort 3 (n=99) (Table 2; cohorts are described in Example 2 and 3). Instead, we investigated if a combination of several microRNAs into prognostic classifiers might improve RFS time prediction over single microRNAs. Data were analyzed in parallel by to statistical methods: 1) leave one out cross validation (LOOCV; Table 1) and 2) combination (weighted models and ratio-based models) of the 11 microRNAs significant in univariate Cox regression analysis in cohort 1 (Table 2) (both methods as described in the methods section). Using these two methods, a list of 13 microRNA candidates with prognostic potential was discovered (Table 3).

Building of a LOOCV Classifier:

Method 1):

We investigated if combinations of several microRNAs might increase the accuracy of predicting BCR risk after RP. Accordingly, we used the normalized expression data for 236 microRNAs detected in more than 70% of the samples in cohort 1. We build a maximum-likelihood prognostic microRNA classifier in order to distinguish the 70 patients without recurrence from the 57 patients with recurrence. A classifier comprising 8 microRNAs was most accurate for classification of the RP samples into no recurrence/recurrence groups (Table 1). Thus, miR-615-3p, miR-185-5p, miR-23a-3p, miR-374b-5p, miR-193a-5p, miR-221-3p, miR-106a-5p, and miR-152-3p were used in at least 70% of the cross-validation loops and constituted the final 8-microRNA prognostic classifier:

Classifier 1. 8-microRNA Classifier (Based on Leave One Out Cross Validation)

The 8-microRNA prognostic classifier identified by method 1) miR-615-3p, miR-185-5p, miR-23a-3p, miR-374b-5p, miR-193a-5p, miR-221-3p, miR-106a-5p, and miR-152-3p (Table 1), correctly classified 74.6% of the recurrent vs. non-recurrent samples in Cohort 1 (P<0.0001, $Chi^2$ test).

To evaluate the performance of the 8-microRNA prognostic classifier for prediction of time to BCR (rather than BCR status), we calculated a weighted sum of the expression of all 8 microRNAs in the prognostic classifier. Next, to assess the prognostic value of the 8-miRNA prognostic classifier, we performed PSA-based RFS analysis. In cohort 1, the prognostic classifier (analyzed as a continuous variable of the weighted sum) was significantly associated with short RFS time in univariate Cox regression analysis (P<0.001; Table 4, top). The 8-miRNA prognostic classifier remained significant in a multivariate model together with Gleason score, surgical margin status, and preoperative PSA (P<0.001; Table 4, top). Notably, when the 8-miRNA prognostic classifier was added to multivariate models including clinicopathological factors only, predictive accuracies increased from 0.73 to 0.79 in cohort 1, suggesting a moderately improved performance of the combined prognostic model. Finally, Kaplan-Meier analyses demonstrated a significant association between the 8-miRNA prognostic classifier and short RFS in cohort 1 (FIG. 1A; P<0.0001, log-rank test).

In conclusion, we constructed an 8-miRNA prognostic classifier, which was a significant independent prognostic predictor of BCR after RP in cohort 1.

Building of Reduced Classifier

Classifier 2: 3-microRNA Classifier (Reduced 8-miRNA Prognostic Classifier Generated from the 8-microRNA Classifier Above)

Using a stepwise exclusion of the 8 microRNAs in Table 1, we identified a 3-microRNA combination of miR-152-3p, miR-185-5p and miR-221-3p. The combined weighted sum of these 3 microRNAs was as the 8-microRNA prognostic classifier significant in both uni- and multivariate Cox regression analyses (Table 5, top). The reduced 8-miRNA prognostic classifier remained significant in a multivariate model together with Gleason score and surgical margin status (P<0.013; Table 5, top). Furthermore, when the reduced 8-miRNA prognostic classifier was added to multivariate models including clinicopathological factors only, predictive accuracies increased from 0.69 to 0.72 in cohort 1, suggesting a moderately improved performance of the combined prognostic model. Finally, Kaplan-Meier analyses demonstrated a significant association between the reduced 8-miRNA prognostic classifier and short RFS in cohort 1 (FIG. 2A; P=0.0001, log-rank test). In conclusion, we constructed a reduced 8-miRNA prognostic classifier, which was a significant independent prognostic predictor of BCR after RP in cohort 1

Building of a Classifier by Univariate Cox Regression Analysis:

Method 2):

By univariate Cox regression analysis of microRNAs expression (analyzed as continuous variables) in cohort 1 (training cohort, n=126), short RFS time was statistically significantly (P values ranging from P=0.049 to P<0.001)

associated with the expression of 11 of the 45 microRNAs tested (Table 2). Thus, high expression of miR-10b-5p, miR-23a-3p, miR-185-5p, miR-615-3p, and miR-625-3p, as well as low expression of miR-30d-3p, miR-133a-3p, miR-193a-5p, miR-221-3p, miR-326, and miR-374b-5p were significantly associated with early BCR. In addition, the established routine clinicopathological prognostic factors: high PSA, high Gleason score, advanced T-stage, and positive surgical margin status were significantly associated with RFS, indicating that our cohort is representative (Table 2). We then investigated whether a combination of the 11 microRNAs might improve prediction of time to RFS over single miRNAs. We used two different approaches to train prognostic miRNA classifiers from the 11 miRNAs significant in univariate Cox regression analysis in the training cohort. In one approach, each miRNA included in the classifier was weighed by the estimated regression coefficients in the multivariate Cox proportional hazards model, and a combined weighted sum for the miRNA classifier was calculated. In the second approach, ratio-based miRNA classifiers were generated based on raw Cq values for each miRNA included in the model.

Classifier 3: 3-microRNA Classifier (Classifier Based on Weighted Sum of microRNAs Significant in Univariate Cox Regression Analysis)

Using stepwise exclusion, we identified a combination of 3 microRNAs; miR-185-5p miR-221-3p, and miR-326 (analyzed as a combined weighted sum of these 3 microRNAs) significantly associated with short RFS time in univariate Cox regression analysis in cohort 1 (P<0.001) and remained significant (P=0.031) also in a multivariate model adjusted for pT stage, Gleason score, surgical margin status, and preoperative PSA (Table 6, top). Notably, addition of the 3-microRNA prognostic classifier to a multivariate model including clinicopathological factors only, increased the predictive accuracy (estimated by Harrell's C-index) from 0.72 to 0.74 in cohort 1 (Table 3, top), suggesting moderately improved performance. Furthermore, Kaplan-Meier analyses showed a significant association between the 3-microRNA prognostic classifier and RFS in cohort 1 (P=0.0005, log-rank test, FIG. 3A). In summary, we have successfully trained and tested a novel 3-microRNA prognostic classifier (miR-185-5p+miR-221-3p+miR-326) that predicted time to BCR after RP independently of routine clinicopathological parameters in cohort 1.

Classifier 4: 4-microRNA Classifier (Based on Ratios of Four microRNAs of the 11 microRNAs Significant in Univariate Cox Regression Analysis)

Biomarker candidates based on ratios of the raw Cq values of the microRNAs would be favorable in a clinical test, because it avoids the dependence on normalization factors. The 11 microRNAs significant in univariate analysis in cohort 1 (Table 2) were used to construct ratio-based microRNA biomarker candidates. We aimed to construct a simple 2:2 miRNA ratio based model from a subset of the 11 candidate miRNAs that were significant in univariate RFS analysis in cohort 1 (Table 2). To ensure robustness of the ratio model, we prioritized miRNAs that were expressed in at least 125 of the 126 RP samples in cohort 1 (training) and which had the lowest Cq values. Furthermore, to increase the dynamic range, we separated up- and downregulated miRNAs in the denominator and numerator. Using these criteria, we developed a 4-miRNA prognostic ratio model (miR-10b-5p×miR-232-3p)/(miR-133a-3p×miR-374b-5p) that was significantly associated with early BCR in cohort 1 by Kaplan-Meier (P<0.0001; FIG. 4A) as well as by uni- (P<0.001) and multivariate (P=0.001) Cox regression analysis (Table 7, top). Furthermore, when the 4-microRNA prognostic ratio model was added to multivariate models including clinicopathological factors only, predictive accuracies increased from 0.73 to 0.76 in cohort 1, suggesting a moderately improved performance of the combined prognostic model.

In conclusion, we constructed a 4-microRNA prognostic ratio model, which was a significant independent prognostic predictor of BCR after RP in cohort 1.

Building of Reduced Ratio Model

Classifier 5: 2-microRNA Classifier (Based on Ratios of Only Two microRNAs Reduced from the 4-microRNA Classifier Above)

The 4-microRNA ratio based classifier above was further reduced to simplify this model for potential future clinical use, it was reduced to a 2-miRNA ratio model (miR-10b-5p/miR-374b-5p). In cohort 1, this 2-miRNA prognostic ratio model was a significant predictor of time to BCR in univariate (P=0.001) as well as multivariate (P<0.001) Cox regression analysis including routine clinicopathological variables (Table 8, top). Notably, addition of the 2-miRNA prognostic ratio model to a multivariate model including clinicopathological factors only, increased the predictive accuracy (estimated by Harrell C-index) from 0.73 to 0.77 in cohort 1, suggesting improved performance. Finally, Kaplan-Meier analyses also demonstrated a significant association between the 2-miRNA prognostic ratio model and RFS time in cohort 1 (P=0.0259; log-rank test; FIG. 5A).

In conclusion, we have constructed a 2-miRNA prognostic ratio model, which was a significant independent predictor of time to BCR after RP in cohort 1.

Conclusion

We have built prognostic classifiers comprising 2-8 microRNAs that predicted time to BCR after RP in a large prostate cancer cohort independently of routine clinicopathological variables.

EXAMPLE 2

Validation of the 8-microRNA Prognostic Classifier for Prediction of Recurrence Risk in an External Validation Cohort Aim of Study To validate the 8-microRNA classifier, described in Example 1) in an independent RP patient cohort.

Methods

Specimens and miRNA Expression Data

We investigated performance of the prognostic potential of the prognostic 8-microRNA classifier in the external GSE21036 microRNA expression dataset from Taylor et al available at the GEO website (14+Hieronymus H, Schultz N, Gopalan A, Carver B S, Chang M T, Xiao Y, et al. Copy number alteration burden predicts prostate cancer relapse. Proc Natl Acad Sci USA. 2014; 111:11139-44.)

This dataset included 99 snap-frozen RP tissue samples (cohort 3). Expression of 368 microRNAs was measured using Agilent Human microRNA Microarray 2.0 (14+Hieronymus H, Schultz N, Gopalan A, Carver B S, Chang M T, Xiao Y, et al. Copy number alteration burden predicts prostate cancer relapse. Proc Natl Acad Sci USA. 2014; 111:11139-44.)

Statistical Analyses

Statistical analyses were conducted in STATA version 11 (StataCorp, Texas, USA). For all analyses P values <0.05 were considered statistically significant.

Prognostic Accuracy:

Biochemical recurrence (BCR; PSA cut-off ≥0.2 ng/ml, based on local clinical practice) was used as endpoint. Patients not having experienced BCR were censored at their last normal PSA measurement. The prognostic value of the 8-microRNA classifier microRNA expression was evaluated by Kaplan-Meier analysis and two-sided log-rank test, and by univariate and multivariate Cox regression analyses as continuous as well as dichotomous variables. For validation of the 8-microRNA classifier, patients in cohort 3 were divided into two groups using the cut-off (fraction) defined in cohort 1 (cut-off value determined afterROC analysis of no recurrence/recurrence status). The proportional hazards assumption was verified by the log-negative-log survival distribution function for all variables. For multivariate testing, all clinicopathological parameters significant in univariate analysis were included. Variables failing the multivariate analysis were excluded from the final multivariate model through stepwise backward selection. Pathological T-stage was dichotomized in localized (T2) and locally advanced disease (T3-4). Gleason score was grouped in two categories containing scores 5-6 (low) and 7-10 (high), respectively. Surgical margin status was dichotomized in negative and positive margins. Preoperative PSA levels were analyzed as a continuous variable. Prognostic accuracy was estimated using Harrell's Concordance Index.

Result

Despite the fact that tumor samples in cohort 3 were of different national origin (U.S.), sampled in a different manner (snap-frozen), subjected to different RNA extraction procedures, analyzed by a different microRNA expression detection platform, and different cohort characteristics (cohort 3 was generally less aggressive and had fewer events of recurrence than cohort 1), our 8-microRNA prognostic classifier performed equally well on the external cohort, underlining the robustness of this 8-microRNA prognostic classifier.

In cohort 3, high molecular risk status, as defined by the 8-miRNA prognostic classifier, was significantly associated with early BCR after RP in both univariate (P=0.003) and multivariate (P=0.006) Cox regression analysis (Table 4, bottom). In this cohort, pathological T-stage did not have significant independent prognostic value, and Gleason score was omitted from analysis due to no events in one of the groups.

Moreover, the predictive accuracy of the multivariate model was estimated by Harrell C-index. Notably, when the 8-microRNA prognostic classifier was added to multivariate models including clinicopathological factors only, predictive accuracies increased from 0.73 to 0.80 in cohort 3 (Table 4, bottom), supporting a moderately improved performance of the combined prognostic model. Finally, Kaplan-Meier analyses demonstrated a significant association between the 8-microRNA prognostic classifier and short RFS in cohort 3 (FIG. 1 bottom; P<0.019, log-rank test).

Conclusion

In conclusion, we have constructed an 8-microRNA prognostic classifier, which was a significant independent prognostic predictor of BCR after RP in two independent patient cohorts (Example 1 and 2). The performance of the 8-microRNA prognostic classifier; a significant independent prognostic predictor of BCR after RP in cohort 1 was validated in an entirely different patient cohort 3, proving the strength of the classifier as a prognostic tool for prostate cancer.

EXAMPLE 3

Validation of a Prognostic Reduced 8-miRNA Prognostic Classifier for Prediction of Recurrence Risk in Two Independent Validation Cohorts Aim of Study To validate the 3-microRNA classifier (miR-152-3p× miR-185-5p×miR-221-3p); which is the reduced classifier from the 8-microRNA classifier described in Example 1 and 2), in two independent RP patient cohorts: Cohort 2 and cohort 3.

Methods

Specimens

Two cohorts were used for validation. Cohort2: For miRNA profiling by RT-qPCR, we used formalin-fixed paraffin-embedded (FFPE) prostate tissue samples. All samples were collected at Department of Urology and obtained from Institute of Pathology, Aarhus University Hospital, Denmark (from 1997-2005). For cancer samples, representative regions with >90% tumor were marked on hematoxylin and eosin (H&E) stained sections, and punch biopsies were taken from the corresponding FFPE blocks for RNA extraction as described in (Haldrup 2013). Total RNA was isolated from 1.5 mm punch biopsies using the miRNeasy FFPE Kit (Qiagen), according to the manufacturer's instructions. The 260/280 nm absorbance ratio (optimal ratio: 2.0) was used as quality assurance for the RNA samples. RNA samples with a ratio<1.75 were excluded from further analysis. The purified RNA was stored at −80° C. This validation cohort (cohort 2) consisted of 112 curatively intended RPs of histologically verified clinically localized prostate cancer (For RFS analyses n=110; two of the 112 RP patients was excluded in the RFS analyses due to postoperative endocrine treatment). Cohort 3: Consists of an external GSE21036 microRNA expression dataset from Taylor et al. available at the GEO website (14+ Hieronymus H, Schultz N, Gopalan A, Carver B S, Chang M T, Xiao Y, et al. Copy number alteration burden predicts prostate cancer relapse. Proc Natl Acad Sci USA. 2014; 111:11139-44.). This dataset included 99 snap-frozen RP tissue samples. Expression of 368 microRNAs was measured using Agilent Human microRNA Microarray 2.0.

MicroRNA Expression Profiling

MicroRNA expression profiling (all reagents from Exiqon) was performed at Exiqon A/S, Vedbaek, Denmark, using the miRCURY LNA™ Universal RT microRNA PCR platform. In brief, 40 ng total RNA was reverse transcribed in 40 µl reactions using the miRCURY LNA™ microRNA PCR, Polyadenylation and cDNA synthesis kit II. cDNA was diluted 100× and analyzed in 10 µl PCR reactions. For cohort 2 (validation), 94 selected miRNAs (including normalization gene miR-151a-5p) were analyzed using a miR-CURY LNA™ Universal RT Pick-&-Mix microRNA PCR panel (4×96 in 384-well, Ready-to-Use). Negative controls (no template in reverse transcription reaction) were run in parallel. Amplification was performed using the LightCycler® 480 Real-Time PCR System (Roche) and ExiLENT SYBR® Green master mix. Amplification curves were analyzed using the Roche LC software for determination of quantification cycle (Cq) values (by the 2nd derivative method {Livak, 2001) and for melting curve analyses. MicroRNAs detected with <3 Cq less than the negative control or for which all Cq values exceeded 37 in all samples were excluded from further analyses (cohort 2: no miRNAs).

Normalization was performed using the normalization gene miR-151a-5p—established to be an optimally stable single normalization gene in Example 1, identified by the NormFinder algorithm (10) as an optimally stable single normalization gene in both cohorts 1 and 2. Normalization was done according to the formula $\Delta Cq = Cq_{Normalisation\ factor} - Cq_{miRNA}$. Differences in expression levels are calculated as $\Delta\Delta Cq = \Delta Cq_{group\ 1} - \Delta Cq_{group\ 2}$. To convert this to fold change, the formula $2^{-\Delta\Delta Cq}$ is used. The reciprocal number, multiplied by a factor of −1, was used for down-regulated miRNAs.

Statistical Analysis:

Statistical analyses were conducted in STATA version 11 (StataCorp, Texas, USA). For all analyses P values <0.05 were considered statistically significant.

Prognostic Accuracy:

Biochemical recurrence (BCR; PSA cut-off ng/ml, based on local clinical practice) was used as endpoint. Patients not having experienced BCR were censored at their last normal PSA measurement. The prognostic value of the classifier was evaluated by Kaplan-Meier analysis and two-sided log-rank test, and by univariate and multivariate Cox regression analyses as continuous as well as dichotomous variable. For validation of the classifier, patients in cohort 2 and 3 were divided into two groups using the cut-off (fraction) defined in cohort 1 (cut-off value determined after ROC analysis of no recurrence/recurrence status). The proportional hazards assumption was verified by the log-negative-log survival distribution function for all variables. For multivariate testing, all clinicopathological parameters significant in univariate analysis were included. Variables failing the multivariate analysis were excluded from the final multivariate model through stepwise backward selection. Pathological T-stage was dichotomized in localized (T2) and locally advanced disease (T3-4). Gleason score was grouped in two categories containing scores 5-6 (low) and 7-10 (high), respectively. Surgical margin status was dichotomized in negative and positive margins. Preoperative PSA levels were analyzed as a continuous variable. Prognostic accuracy was estimated using Harrell's Concordance Index.

Results

As seen in Table 5, high molecular risk status, as defined by the reduced 8-miRNA prognostic classifier, was significantly associated with early BCR after RP in both univariate (P=0.001) and multivariate (P=0.003) Cox regression analysis in cohort 3 (Table 5, bottom). In this cohort, the preoperative PSA level did not have significant independent prognostic value, and Gleason score was omitted from analysis due to no events in one of the groups. Moreover, the reduced 8-miRNA prognostic classifier was significantly associated with early BCR after RP in univariate (P=0.047) and borderline significant in multivariate (P=0.091) Cox regression analysis in cohort 2 (Table 5, middle). In this cohort, pathological T-stage and Gleason score did not have significant independent prognostic value either.

Furthermore, the predictive accuracy of each of the multivariate models was estimated by Harrell C-index. Interestingly, when the reduced 8-miRNA prognostic classifier was added to multivariate models including clinicopathological factors only, predictive accuracies increased from 0.74 to 0.78 in cohort 3 (Table 5, bottom) and 0.71 to 0.73 in cohort 2 (Table 5, middle), supporting a moderately improved performance of the combined prognostic model. Finally, Kaplan-Meier analyses demonstrated a significant association between the reduced 8-miRNA prognostic classifier and short RFS in cohort 2 (FIG. 2B; P=0.014, log-rank test) and this association was also successfully validated in cohort 3 (FIG. 2C; P=0.019, log-rank test).

Despite the fact that tumor samples in cohort 3 were of different national origin (U.S.), sampled in a different manner (snap-frozen), subjected to different RNA extraction procedures, analyzed by a different microRNA expression detection platform, and different cohort characteristics (cohort 3 was generally less aggressive and had fewer events of recurrence than cohort 1 and 2), reduced 8-miRNA prognostic classifier performed equally well on the external cohort, underlining the robustness of this reduced 8-miRNA prognostic classifier.

Conclusion

We have constructed a reduced 8-miRNA prognostic classifier, which was a significant prognostic predictor of time to BCR after RP in three independent patient cohorts (Example 1 and 3). The performance of the reduced 8-miRNA prognostic classifier; a significant independent prognostic predictor of time to BCR after RP in cohort 1 was validated in an entirely different patient cohort 3, proving the strength of the classifier as a prognostic tool for prostate cancer.

EXAMPLE 4

Validation of a Prognostic 3-microRNA Classifier for Prediction of Recurrence Risk in Two Independent Validation Cohorts Aim of Study To validate the 3-microRNA classifier (miR-185-5p+miR-221-3p+miR-326-based on weighted sum of miRNAs significant in univariate Cox regression analysis, described in Example 1) in two independent patient cohorts: Cohort 2 and cohort 3.

Methods

Described in Example 3

Results

As seen in Table 6, the prognostic value of the 3-microRNA classifier was successfully validated by univariate as well as multivariate Cox regression analyses in cohort 2 and cohort 3. High molecular risk status, as defined by the 3-miRNA prognostic classifier, was significantly associated with early BCR after RP in both univariate (P=0.006 and P<0.001) and multivariate (P=0.048 and P=0.012) Cox regression analysis in cohort 2 and cohort 3, respectively (Table 6, middle and bottom). In cohort 2, the surgical margin status and Gleason score did not have significant independent prognostic value, and in cohort 3, the pathological T stage was not significant in the multivariate model, and Gleason score was omitted from analysis due to no events in one of the groups.

Moreover, the predictive accuracy of each of the multivariate models was estimated by Harrell C-index. Notably, when the 3-microRNA prognostic classifier was added to multivariate models including clinicopathological factors only, predictive accuracies increased from 0.73 to 0.75 in cohort 3 (Table 6, middle) and 0.74 to 0.80 in cohort 3 (Table 5, bottom), supporting an improved performance of the combined prognostic model. Finally, Kaplan-Meier analyses demonstrated a significant association between the 3-microRNA prognostic classifier and short RFS in cohort 2 (FIG. 3B; P=0.035, log-rank test) and this association was also successfully validated in cohort 3 (FIG. 3C; P=0.008, log-rank test).

Despite the fact that tumor samples in cohort 3 were of different national origin (U.S.), sampled in a different manner (snap-frozen), subjected to different RNA extraction procedures, analyzed by a different microRNA expression detection platform, and different cohort characteristics (cohort 3 was generally less aggressive and had fewer events of recurrence than cohort 1 and 2), our 3-microRNA prognostic classifier performed equally well on the external cohort, underlining the robustness of this 3-microRNA prognostic classifier.

Conclusion

We have constructed a 3-microRNA prognostic classifier with significant independent prognostic predicting value for predicting time to BCR after RP in three independent patient cohorts (Example 1 and 4). The performance of the 3-microRNA prognostic classifier; a significant independent prognostic predictor of time to BCR after RP in cohort 1 was validated in an entirely different patient cohort 3, proving the strength of the classifier as a prognostic tool for prostate cancer.

EXAMPLE 5

Validation of a Prognostic 4-microRNA (Ratio Based) Classifier for Prediction of Recurrence Risk in an Independent Validation Cohort Aim of Study To validate the ratio-based 4-microRNA classifier (miR-10b-5p×miR-23a-3p/miR-133a-3p×miR-374b-5p, described in Example 1) in two independent patient cohorts: Cohort 2 and cohort 3.

Methods

Described in Example 3

Results

As seen in Table 7, high molecular risk status, as defined by the 4-microRNA prognostic ratio model, was significantly associated with early BCR after RP in both univariate (P=0.021) and multivariate (P=0.024) Cox regression analysis in cohort 2 (Table 7, middle). In this cohort, the pathological T stage and Gleason score did not have significant independent prognostic value. Moreover, the 4-microRNA prognostic ratio model was significantly associated with early BCR after RP in univariate (P=0.014) and borderline significant in multivariate (P=0.115) Cox regression analysis in cohort 3 (Table 7, bottom). In cohort 3, pathological T-stage did not have significant independent prognostic value either, and Gleason score was omitted from analysis due to no events in one of the groups.

Moreover, the predictive accuracy of each of the multivariate models was estimated by Harrell C-index. When the 4-microRNA prognostic ratio model was added to multivariate models including clinicopathological factors only, predictive accuracies increased from 0.73 to 0.75 in cohort 2 (Table 7, middle) and 0.73 to 0.78 in cohort 2 (Table 7, bottom), supporting a moderately improved performance of the combined prognostic model. Finally, Kaplan-Meier analyses demonstrated a significant association between the 4-microRNA prognostic ratio model and short RFS in cohort 2 (FIG. 4B; P=0.0355, log-rank test) and this association was borderline significant in cohort 3 (FIG. 4C; P 30=0.1097, log-rank test).

Conclusion

In conclusion, we have constructed a 4-microRNA prognostic ratio model, which was a significant prognostic predictor of BCR after RP in three independent patient cohorts and with prognostic value independently of routine clinicopathological parameters in two independent prostate cancer patient cohorts (Example 1 and 5).

EXAMPLE 6

Validation of a Prognostic 2-microRNA (Ratio Based) Classifier for Prediction of Recurrence Risk in Two Independent Validation Cohorts Aim of Study To validate the ratio-based 2-microRNA classifier (miR10b-5p/miR-374b-5p, described in Example 1) in two independent patient cohorts: Cohort 2 and cohort 3.

Methods

Described in Example 3

Results

As seen in Table 8, the prognostic value of the 2-microRNA prognostic ratio model was successfully validated by univariate as well as multivariate Cox regression analyses in cohort 2 and cohort 3. High molecular risk status, as defined by the 2-microRNA prognostic ratio model, was significantly associated with early BCR after RP in both univariate (P=0.047 and P=0.023) and multivariate (P=0.047 and P=0.015) Cox regression analysis in cohort 2 and cohort 3, respectively (Table 8, middle and bottom). In cohort 2, the surgical pathological T stage and Gleason score did not have significant independent prognostic value, and in cohort 3, the pathological T stage was not significant in the multivariate model, and Gleason score was omitted from analysis due to no events in one of the groups.

Moreover, the predictive accuracy of each of the multivariate models was estimated by Harrell C-index. Notably, when the 2-microRNA prognostic ratio model was added to multivariate models including clinicopathological factors only, predictive accuracies increased from 0.73 to 0.74 in cohort 2 (Table 8, middle) and 0.73 to 0.79 in cohort 3 (Table 8, bottom), supporting a moderately improved performance of the combined prognostic model. Finally, Kaplan-Meier analyses demonstrated a significant association between the 2-microRNA prognostic ratio model and short RFS in cohort 2 (FIG. 5B; P 30=0.0487, log-rank test) and this association was also successfully validated in cohort 3 (FIG. 5C; P=0.0005, log-rank test).

Despite the fact that tumor samples in cohort 3 were of different national origin (U.S.), sampled in a different manner (snap-frozen), subjected to different RNA extraction procedures, analyzed by a different microRNA expression detection platform, and different cohort characteristics (cohort 3 was generally less aggressive and had fewer events of recurrence than cohort 1 and 2), our 2-microRNA prognostic ratio model performed equally well on the external cohort, underlining the robustness of this 2-microRNA prognostic ratio model.

CONCLUSION

We have constructed a ratio-based 2-microRNA prognostic classifier with significant independent value for predicting time to BCR after RP in three independent patient cohorts (Example 1 and 6). The performance of the 2-microRNA prognostic ratio model; a significant independent prognostic predictor of time to BCR after RP in cohort 1 was validated in an entirely different patient cohort 3, proving the strength and robustness of the classifier as a prognostic tool for prostate cancer.

TABLE 1

The 8 miRNAs used in at least 70% of the cross validation loops when building the prognostic miRNA classifier. Results from the pairwise comparison of patients without and with recurrence are shown (Example 1).

| Up/down-regulated in recurrence | Cohort 1 (n = 70 vs. n = 57) | | | | Cohort 2 (n = 62 vs. n = 50) | | | | Cohort 3 (n = 74 vs. n = 25) | | | |
|---|---|---|---|---|---|---|---|---|---|---|---|---|
| | FC | P value | BH corrected P value | AUC (95%-CI) | FC | P value | BH corrected P value | AUC (95%-CI) | FC | P value | BH corrected P value | AUC (95%-CI) |
| miR-615-3p | 2.86 | 0.001 | 0.002 | 0.68 (0.59-0.78) | 1.64 | 0.124 | 0.495 | 0.58 (0.48-0.69) | −1.14 | 0.646 | 0.652 | 0.53 (0.38-0.68) |
| miR-185-5p | 1.54 | 0.002 | 0.002 | 0.68 (0.59-0.78) | 1.12 | 0.631 | 0.804 | 0.53 (0.42-0.64) | 1.16 | 0.019 | 0.115 | 0.66 (0.53-0.78) |
| miR-374b-5p | −1.49 | 0.003 | 0.004 | 0.66 (0.57-0.76) | −1.05 | 0.753 | 0.861 | 0.52 (0.40-0.62) | −1.16 | 0.074 | 0.198 | 0.62 (0.49-0.75) |
| miR-193a-5p | −1.36 | 0.010 | 0.013 | 0.64 (0.54-0.74) | 1.14 | 0.266 | 0.532 | 0.56 (0.45-0.67) | 1.07 | 0.263 | 0.526 | 0.58 (0.45-0.70) |
| miR-23a-3p | 1.19 | 0.008 | 0.013 | 0.64 (0.54-0.74) | −1.16 | 0.215 | 0.532 | 0.57 (0.46-0.68) | 1.08 | 0.652 | 0.652 | 0.53 (0.39-0.67) |
| miR-221-3p | −1.26 | 0.025 | 0.030 | 0.62 (0.52-0.72) | −1.53 | 0.049 | 0.388 | 0.61 (0.50-0.71) | −1.42 | 0.029 | 0.115 | 0.65 (0.52-0.77) |
| miR-106a-5p | −1.26 | 0.028 | 0.031 | 0.61 (0.51-0.72) | −1.05 | 0.704 | 0.804 | 0.52 (0.41-0.63) | −1.18 | 0.535 | 0.652 | 0.54 (0.40-0.68) |
| miR-152-3p | −1.39 | 0.069 | 0.069 | 0.58 (0.48-0.68) | −1.09 | 0.648 | 0.804 | 0.53 (0.42-0.63) | 1.06 | 0.421 | 0.652 | 0.55 (0.41-0.69) |

AUC, area under the curve of ROC analysis;
CI, confidence interval;
FC: Fold change calculated based on the mean difference between the two groups.
The reciprocal number multiplied by −1 was used for downregulated miRNAs.
P values were calculated with Wilcoxon signed-rank test, and adjusted for multiple testing by the Benjamini-Hochberg (BH) method.
P < 0.05 was considered significant and marked in bold.

TABLE 2

Univariate Cox regression analyses of biochemical recurrence-free survival time (Example 1). Significant miRNAs from cohort 1 were tested in cohorts 2 and 3.

| Variable | Characteristics | Cohort 1, n = 126, 56 with recurrence | | | | Cohort 2, n = 110, 49 with recurrence |
|---|---|---|---|---|---|---|
| | | HR (95% CI) | P value | BH corrected P value | C-index[a] | HR (95% CI) |
| Age at diagnosis | Continuous | 1.00 (0.94-1.05) | 0.858 | 0.815 | 0.53 | 0.97 (0.93-1.03) |
| Tumor stage | pT2a-c vs. pT3a-c | 3.12 (1.81-5.36) | <0.001 | 0.001 | 0.64 | 3.00 (1.69-5.30) |
| Gleason score | 5-6 vs. 7-10 | 2.72 (1.51-4.93) | 0.001 | 0.010 | 0.61 | 2.42 (1.23-4.73) |
| Surgical margin status | Negative vs. positive | 2.73 (1.59-4.70) | <0.001 | 0.001 | 0.63 | 3.37 (1.89-6.00) |
| Preoperative PSA | Continuous | 1.05 (1.02-1.08) | <0.001 | 0.001 | 0.62 | 1.05 (1.03-1.07) |
| miR-374b-5p | Continuous | 0.72 (0.60-0.86) | <0.001 | 0.005 | 0.63 | 1.02 (0.83-1.25) |
| miR-23a-3p | Continuous | 2.57 (1.43-4.63) | 0.002 | 0.017 | 0.63 | 0.80 (0.56-1.13) |
| miR-625-3p | Continuous | 1.22 (1.06-1.40) | 0.006 | 0.043 | 0.57 | 0.92 (0.82-1.04) |
| miR-615-3p | Continuous | 1.16 (1.04-1.28) | 0.007 | 0.044 | 0.63 | 1.04 (0.94-1.16) |
| miR-185-5p | Continuous | 1.47 (1.10-1.97) | 0.009 | 0.050 | 0.64 | 1.06 (0.85-1.33) |
| miR-133a-3p | Continuous | 0.80 (0.57-0.96) | 0.017 | 0.085 | 0.57 | 0.78 (0.66-0.92) |
| miR-193a-5p | Continuous | 0.78 (0.62-0.97) | 0.025 | 0.114 | 0.60 | 0.98 (0.78-1.24) |
| miR-221-3p | Continuous | 0.68 (0.49-0.96) | 0.029 | 0.121 | 0.55 | 0.83 (0.69-0.98) |
| miR-326 | Continuous | 0.90 (0.82-0.99) | 0.032 | 0.123 | 0.57 | 0.91 (0.84-0.99) |
| miR-10b-5p | Continuous | 1.28 (1.00-1.63) | 0.046 | 0.163 | 0.57 | 1.26 (0.93-1.71) |
| miR-30d-3p | Continuous | 0.89 (0.79-1.00) | 0.049 | 0.163 | 0.57 | 0.91 (0.81-1.03) |

| Variable | Cohort 2, n = 110, 49 with recurrence | | | Cohort 3, n = 99, 25 with recurrence | | | |
|---|---|---|---|---|---|---|---|
| | P value | BH corrected P value | C-index[a] | HR (95% CI) | P value | BH corrected P value | C-index[a] |
| Age at diagnosis | 0.319 | 0.425 | 0.53 | 1.03 (0.98-1.10) | 0.278 | 0.379 | 0.56 |
| Tumor stage | <0.001 | 0.001 | 0.64 | 4.05 (1.80-9.12) | 0.001 | 0.005 | 0.68 |
| Gleason score | 0.010 | 0.032 | 0.59 | — | — | — | — |
| Surgical margin status | <0.001 | 0.001 | 0.64 | 3.81 (1.70-8.54) | 0.001 | 0.005 | 0.63 |
| Preoperative PSA | <0.001 | 0.001 | 0.72 | 1.09 (1.06-1.13) | <0.001 | 0.002 | 0.66 |
| miR-374b-5p | 0.831 | 0.878 | 0.55 | 0.57 (0.31-1.03) | 0.062 | 0.133 | 0.62 |
| miR-23a-3p | 0.205 | 0.298 | 0.54 | 1.33 (0.60-2.94) | 0.476 | 0.549 | 0.50 |
| miR-625-3p | 0.172 | 0.278 | 0.56 | 0.71 (0.41-1.24) | 0.227 | 0.378 | 0.53 |
| miR-615-3p | 0.439 | 0.540 | 0.53 | 1.00 (0.78-1.27) | 0.973 | 0.973 | 0.50 |
| miR-185-5p | 0.610 | 0.697 | 0.52 | 4.59 (1.52-13.90) | 0.007 | 0.021 | 0.65 |
| miR-133a-3p | 0.003 | 0.012 | 0.62 | 0.74 (0.48-1.14) | 0.174 | 0.326 | 0.57 |
| miR-193a-5p | 0.878 | 0.878 | 0.52 | 1.43 (0.65-3.16) | 0.374 | 0.468 | 0.57 |
| miR-221-3p | 0.033 | 0.075 | 0.56 | 0.59 (0.41-0.86) | 0.005 | 0.019 | 0.67 |

TABLE 2-continued

Univariate Cox regression analyses of biochemical recurrence-free survival time (Example 1). Significant miRNAs from cohort 1 were tested in cohorts 2 and 3.

| miR-326 | 0.023 | 0.061 | 0.61 | 1.45 (0.76-2.83) | 0.256 | 0.379 | 0.54 |
|---|---|---|---|---|---|---|---|
| miR-10b-5p | 0.135 | 0.270 | 0.53 | 1.12 (0.65-1.90) | 0.690 | 0.739 | 0.50 |
| miR-30d-3p | 0.174 | 0.278 | 0.55 | 1.79 (1.09-2.92) | 0.020 | 0.050 | 0.68 |

[a]Predictive accuracy, estimated by Harrell's concordance index (C-index).
CI: Confidence Interval,
HR: Hazard ratio,
PSA: Prostate specific antigen.
Significant P values (P < 0.05) are marked in bold.
P values of individual miRNAs were adjusted for multiple testing by the Benjamini-Hochberg (BH) method,
FDR <0.2 was considered significant (marked in bold).

TABLE 3

Combined list of microRNAs with potential prognostic value from which classifiers are build.

| Combined microRNA discovery | Discovery method 1 (leave one out cross validation) | | Discovery Method 2 (Cox Regression) | | | |
|---|---|---|---|---|---|---|
| | 8 microRNA classifier (1)[a] | Reduced 8-miRNA prognostic classifier (2)[a] | 11 microRNAs with prognostic potential | 3 microRNA classifier (3)[a] | 4 microRNA classifier (ratio based) (4)[a] | 2 microRNA classifier (ratio based) (5)[a] |
| miR-374b-5p | miR-374b-5p | | miR-374b-5p | | miR-374b-5p | miR-374b-5p |
| miR-23a-3p | miR-23a-3p | | miR-23a-3p | | miR-23a-3p | |
| miR-625-3p | | | miR-625-3p | | | |
| miR-615-3p | miR-615-3p | | miR-615-3p | | | |
| miR-185-5p | miR-185-5p | miR-185-5p | miR-185-5p | miR-185-5p | | |
| miR-133a-3p | | | miR-133a-3p | | miR-133a-3p | |
| miR-193a-5p | miR-193a-5p | | miR-193a-5p | | | |
| miR-221-3p | miR-221-3p | miR-221-3p | miR-221-3p | miR-221-3p | | |
| miR-326 | | | miR-326 | miR-326 | | |
| miR-10b-5p | | | miR-10b-5p | | miR-10b-5p | miR-10b-5p |
| miR-30d-3p | | | miR-30d-3p | | | |
| miR-152-3p | miR-152-3p | miR-152-3p | | | | |
| miR-106a-5p | miR-106a-5p | | | | | |

[a]Corresponds to the listing in Example 1.

TABLE 4

8-miRNA prognostic classifier (Example 1 + 2). Prognostic potential of the 8-miRNA prognostic classifier assessed by uni- and multivariate Cox regression analyses of biochemical recurrence-free survival time in three RP cohorts.

| Variable | Characteristics | Univariate | | | Multivariate-Final[c] | | |
|---|---|---|---|---|---|---|---|
| | | HR (95% CI) | P value | C-index[a] | HR (95% CI) | P value | C-index[b] |
| Cohort 1, n = 126, 56 recurrence | | | | | | | |
| Age at diagnosis | Continuous | 1.00 (0.94-1.05) | 0.858 | 0.53 | — | — | |
| Tumor stage | pT2a-c vs. pT3a-c | 3.12 (1.81-5.36) | <0.001 | 0.64 | — | — | |
| Gleason score | 5-6 vs. 7-10 | 2.73 (1.51-4.93) | 0.001 | 0.61 | 1.94 (1.03-3.69) | 0.042 | 0.73  0.79 |
| Surgical margin status | Negative vs. positive | 2.73 (1.59-4.70) | <0.001 | 0.63 | 2.91 (1.65-5.12) | <0.001 | |
| Preoperative PSA | Continuous | 1.05 (1.02-1.08) | <0.001 | 0.62 | 1.03 (1.01-1.07) | 0.005 | |
| 8-miRNA prognostic classifier[d] | Continuous | 2.24 (1.97-3.75) | <0.001 | 0.74 | 2.02 (1.52-2.68) | <0.001 | |
| Cohort 2, n = 110, 49 recurrence | | | | | | | |
| Age at diagnosis | Continuous | 0.97 (0.93-1.03) | 0.319 | 0.53 | — | — | |
| Tumor stage | pT2a-c vs. pT3a-c | 3.00 (1.69-5.30) | <0.001 | 0.63 | — | — | |
| Gleason score | 5-6 vs. 7-10 | 2.42 (1.23-4.73) | 0.010 | 0.59 | | | |
| Surgical margin status | Negative vs. positive | 3.37 (1.89-6.00) | <0.001 | 0.64 | 3.24 (1.81-5.82) | <0.001 | 0.71 |
| Preoperative PSA | Continuous | 1.05 (1.03-1.07) | <0.001 | 0.72 | 1.05 (1.03-1.07) | <0.001 | |
| 8-mRNA prognostic classifier[d] | Continuous | 0.97 (0.73-1.28) | 0.817 | 0.52 | — | — | |

TABLE 4-continued 8-miRNA prognostic classifier (Example 1 + 2). Prognostic potential of the 8-miRNA prognostic classifier assessed by uni- and multivariate Cox regression analyses of biochemical recurrence-free survival time in three RP cohorts.

| Variable | Characteristics | Univariate | | | Multivariate-Final[c] | | |
|---|---|---|---|---|---|---|---|
| | | HR (95% CI) | P value | C-index[a] | HR (95% CI) | P value | C-index[b] |
| Cohort 3, n = 99, 25 recurrence* | | | | | | | |
| Age at diagnosis | Continuous | 1.03 (0.98-1.09) | 0.278 | 0.56 | — | — | |
| Tumor stage | pT2a-c vs. pT3a-c | 4.05 (1.80-9.12) | 0.001 | 0.68 | — | — | |
| Surgical margin status | Negative vs. positive | 3.81 (1.70-8.54) | 0.001 | 0.63 | 2.94 (1.29-6.72) | 0.011 | 0.73  0.80 |
| Preoperative PSA | Continuous | 1.09 (1.06-1.13) | <0.001 | 0.66 | 1.09 (1.04-1.13) | <0.001 | |
| 8-miRNA prognostic classifier[d] | Continuous | 1.86 (1.23-2.81) | 0.003 | 0.66 | 1.88 (1.20-2.96) | 0.006 | |

Abbreviations: CI, confidence Interval; HR, hazard ratio; PSA, prostate specific antigen; pT, pathological tumor stage; RP, radical prostatectomy.
[a]Predictive accuracy estimated by Harrell's concordance index (C-index).
[b]Left column, C-index based on clinicopathological variables only (i.e. excluding miRNA classifier expression); right column, C-index based on all variables included in the model.
[c]The 8-miRNA prognostic classifier was analyzed in multivariate analysis including tumor stage, Gleason score, surgical margin, and preoperative PSA. In the final multivariate model, variables failing the global multivariate analysis were excluded by stepwise backward selection.
[d]For generation of this 8-miRNA prognostic classifier, a weighted sum was calculated. The expression level of each miRNA was weighed by the estimated regression coefficients in a multivariate proportional hazards model (trained in cohort 1, and tested in cohorts 2 and 3).
*Gleason score was excluded from analysis in cohort 3, because the low Gleason score group (5-6) had no events, causing error in the analysis.
Significant P values (P < 0.05) are marked in bold.

TABLE 5

Reduced 8-miR classifier (Example 1 + 3): Prognostic potential of the reduced 8-miRNA prognostic classifier (miR-152-3p + miR-185-5p + miR-221-3p) assessed by uni- and multivariate Cox regression analyses of biochemical recurrence-free survival time in three RP cohorts.

| Variable | Characteristics | Univariate | | | Multivariate-Final[c] | | |
|---|---|---|---|---|---|---|---|
| | | HR (95% CI) | P value | C-index[a] | HR (95% CI) | P value | C-index[b] |
| Cohort 1, n = 126, 56 recurrence | | | | | | | |
| Age at diagnosis | Continuous | 1.00 (0.94-1.05) | 0.858 | 0.53 | — | — | |
| Preoperative PSA | ≤10 vs. <10 ng/ml | 1.81 (0.91-3.58) | 0.090 | 0.54 | — | — | |
| Tumor stage | pT2a-c vs. pT3a-c | 3.12 (1.81-5.36) | <0.001 | 0.64 | — | — | |
| Gleason score | 5-6 vs. 7-10 | 2.73 (1.51-4.93) | 0.001 | 0.61 | 2.24 (1.20-3.45) | 0.011 | 0.69  0.72 |
| Surgical margin status | Negative vs. positive | 2.73 (1.59-4.70) | <0.001 | 0.63 | 2.76 (1.59-4.78) | <0.001 | |
| Reduced 8-miRNA prognostic classifier[d] | Continuous | 1.67 (1.26-2.21) | <0.001 | 0.64 | 2.00 (1.16-3.45) | 0.013 | |
| Cohort 2, n = 110, 49 recurrence | | | | | | | |
| Age at diagnosis | Continuous | 0.97 (0.93-1.03) | 0.319 | 0.53 | — | — | |
| Tumor stage | pT2a-c vs. pT3a-c | 3.00 (1.69-5.30) | <0.001 | 0.63 | — | — | |
| Gleason score | 5-6 vs. 7-10 | 2.42 (1.23-4.73) | 0.010 | 0.59 | — | — | |
| Preoperative PSA | ≤10 vs. <10 ng/ml | 3.54 (1.72-7.31) | 0.001 | 0.64 | 3.52 (1.70-7.31) | 0.001 | 0.71  0.73 |
| Surgical margin status | Negative vs. positive | 3.37 (1.89-6.00) | <0.001 | 0.64 | 3.63 (2.01-6.53) | <0.001 | |
| Reduced 8-miRNA prognostic classifier[d] | Continuous | 1.31 (1.00-1.71) | 0.047 | 0.56 | 1.27 (0.96-1.67) | 0.091 | |
| Cohort 3, n = 99, 25 recurrence* | | | | | | | |
| Age at diagnosis | Continuous | 1.03 (0.98-1.09) | 0.278 | 0.56 | — | — | |
| Preoperative PSA | ≤10 vs. <10 ng/ml | 3.67 (1.64-8.20) | 0.002 | 0.64 | — | — | |
| Tumor stage | pT2a-c vs. pT3a-c | 4.05 (1.80-9.12) | 0.001 | 0.68 | 2.91 (1.26-6.72) | 0.012 | 0.74  0.78 |
| Surgical margin status | Negative vs. positive | 3.81 (1.70-8.54) | 0.001 | 0.63 | 3.38 (1.47-7.76) | 0.004 | |
| Reduced 8-miRNA prognostic classifier[d] | Continuous | 1.88 (1.31-2.70) | 0.001 | 0.70 | 1.82 (1.23-2.69) | 0.003 | |

Abbreviations: CI, confidence Interval; HR, hazard ratio; PSA, prostate specific antigen; pT, pathological tumor stage; RP, radical prostatectomy.
[a]Predictive accuracy estimated by Harrell's concordance index (C-index).
[b]Left column, C-index based on clinicopathological variables only (i.e. excluding miRNA classifier expression); right column, C-index based on all variables included in the model
[c]The reduced 8-miRNA prognostic classifier was analyzed in multivariate analysis including tumor stage, Gleason score, surgical margin, and preoperative PSA. In the final multivariate model, variables failing the global multivariate analysis were excluded by stepwise backward selection.
[d]For generation of this reduced 8-miRNA prognostic classifier, a weighted sum was calculated. The expression level of each miRNA was weighed by the estimated regression coefficients in a multivariate proportional hazards model (trained in cohort 1, and tested in cohorts 1 and 3).
*Gleason score was excluded from analysis in cohort 3, because the low Gleason score group (5-6) had no events, causing error in the analysis.
Significant P values (P < 0.05) are marked in bold.

TABLE 6

Combination of single microRNA Cox regression candidates (Example 1 + 4). Prognostic potential of the 3-miRNA prognostic classifier (miR-185-5p + miR-221-3p + miR-326) assessed by uni- and multivariate Cox regression analyses of biochemical recurrence-free survival time in three RP cohorts.

| Variable | Characteristics | Univariate | | | Multivariate-Final[c] | | | |
|---|---|---|---|---|---|---|---|---|
| | | HR (95% CI) | P value | C-index[a] | HR (95% CI) | P value | C-index[b] | |
| Cohort 1, n = 126, 56 recurrence | | | | | | | | |
| Age at diagnosis | Continuous | 1.00 (0.94-1.05) | 0.858 | 0.53 | — | — | | |
| Tumor stage | pT2a-c vs. pT3a-c | 3.12 (1.81-5.36) | <0.001 | 0.64 | — | — | | |
| Gleason score | 5-6 vs.7-10 | 2.73 (1.51-4.93) | 0.001 | 0.61 | 2.68 (1.46-4.93) | 0.001 | | |
| Surgical margin status | Negative vs. positive | 2.73 (1.59-4.70) | <0.001 | 0.63 | 2.46 (1.39-4.34) | 0.002 | 0.72 | 0.74 |
| Preoperative PSA | Continuous | 1.05 (1.02-1.08) | <0.001 | 0.62 | 1.04 (1.01-1.07) | 0.005 | | |
| 3-miRNA classifier[d] | Continuous | 1.71 (1.31-2.24) | <0.001 | 0.66 | 1.36 (1.03-1.79) | 0.031 | | |
| Cohort 2, n = 110, 49 recurrence | | | | | | | | |
| Age at diagnosis | Continuous | 0.97 (0.93-1.03) | 0.319 | 0.53 | — | — | | |
| Surgical margin status | Negative vs. positive | 3.37 (1.89-6.00) | <0.001 | 0.64 | — | — | | |
| Gleason score | 5-6 vs.7-10 | 2.42 (1.23-4.73) | 0.010 | 0.59 | — | — | | |
| Tumor stage | pT2a-c vs. pT3a-c | 3.00 (1.69-5.30) | <0.001 | 0.63 | 3.21 (1.76-5.84) | <0.001 | 0.73 | 0.75 |
| Preoperative PSA | Continuous | 1.05 (1.03-1.07) | <0.001 | 0.72 | 1.05 (1.02-1.07) | <0.001 | | |
| 3-miRNA classifier[d] | Continuous | 1.44 (1.11-1.88) | 0.006 | 0.58 | 1.28 (1.00-1.64) | 0.048 | | |
| Cohort 3, n = 99, 25 recurrence* | | | | | | | | |
| Age at diagnosis | Continuous | 1.03 (0.98-1.09) | 0.278 | 0.56 | — | — | | |
| Tumor stage | pT2a-c vs. pT3a-c | 4.05 (1.80-9.12) | 0.001 | 0.68 | — | — | | |
| Surgical margin status | Negative vs. positive | 3.81 (1.70-8.54) | 0.001 | 0.63 | 2.40 (0.94-6.12) | 0.007 | 0.74 | 0.80 |
| Preoperative PSA | Continuous | 1.09 (1.06-1.13) | <0.001 | 0.66 | 1.06 (1.02-1.11) | 0.008 | | |
| 3-miRNA classifier[d] | Continuous | 2.10 (1.42-3.10) | <0.001 | 0.70 | 1.91 (1.26-2.91) | 0.012 | | |

Abbreviations: CI, confidence Interval; HR, hazard ratio; PSA, prostate specific antigen; pT, pathological tumor stage; RP, radical prostatectomy.
[a]Predictive accuracy estimated by Harrell's concordance index (C-index).
[b]Left column, C-index based on clinicopathological variables only (i.e. excluding miRNA classifier expression); right column, C-index based on all variables included in the model.
[c]The 3-miRNA prognostic classifier was analyzed in multivariate analysis including tumor stage, Gleason score, surgical margin, and preoperative PSA. In the final multivariate model, variables failing the global multivariate analysis were excluded by stepwise backward selection.
[d]For generation of this 3-miRNA prognostic classifier, a weighted sum was calculated. The expression level of each miRNA was weighed by the estimated regression coefficients in a multivariate proportional hazards model (trained in cohort 1, and tested in cohorts 2 and 3).
*Gleason score was excluded from analysis in cohort 3, because the low Gleason score group (5-6) had no events, causing error in the analysis.
Significant P values (P < 0.05) are marked in bold.

TABLE 7

4-miRNA prognostic ratio model (Example 1 + 5). Prognostic potential of 4-miRNA ratio model [miR-10b-5p × miR-23a-3p)/(miR-133a-3p × miR-374b-5p] assessed by uni- and multivariate Cox regression analyses of biochemical recurrence-free survival in three RP cohorts.

| Variable | Characteristics | Univariate | | | Multivariate-Final[c] | | | |
|---|---|---|---|---|---|---|---|---|
| | | HR (95% CI) | P value | C-index[a] | HR (95% CI) | P value | C-index[b] | |
| Cohort 1, n = 126, 56 recurrence | | | | | | | | |
| Age at diagnosis | Continuous | 1.00 (0.94-1.05) | 0.858 | 0.53 | — | — | | |
| Tumor stage | pT2a-c vs. pT3a-c | 3.12 (1.81-5.36) | <0.001 | 0.64 | — | — | | |
| Gleason score | 5-6 vs.7-10 | 2.73 (1.51-4.93) | 0.001 | 0.61 | 1.98 (1.04-3.75) | 0.037 | | |
| Surgical margin status | Negative vs. positive | 2.73 (1.59-4.70) | <0.001 | 0.63 | 3.04 (1.71-5.42) | <0.001 | 0.73 | 0.76 |
| Preoperative PSA | Continuous | 1.05 (1.02-1.08) | <0.001 | 0.62 | 1.04 (1.02-1.07) | 0.002 | | |
| 4-miRNA ratio model | Continuous | 0.77 (0.68-0.87) | <0.001 | 0.69 | 0.78 (0.67-0.90) | 0.001 | | |
| Cohort 2, n = 110, 49 recurrence | | | | | | | | |
| Age at diagnosis | Continuous | 0.97 (0.93-1.03) | 0.319 | 0.53 | — | — | | |
| Tumorstage | pT2a-c vs. pT3a-c | 3.00 (1.69-5.30) | <0.001 | 0.63 | — | — | | |
| Gleasonscore | 5-6 vs.7-10 | 2.42 (1.23-4.73) | 0.010 | 0.59 | — | — | | |
| Surgical margin status | Negative vs. positive | 3.37 (1.89-6.00)) | <0.001 | 0.64 | 3.11 (1.71-5.68) | <0.001 | 0.73 | 0.75 |
| Preoperative PSA | Continuous | 1.05 (1.03-1.07) | <0.001 | 0.72 | 1.05 (1.03-1.07) | <0.001 | | |
| 4-miRNA ratio model | Continuous | 0.81 (0.67-0.97) | 0.021 | 0.57 | 0.81 (0.66-0.97) | 0.024 | | |
| Cohort 3, n = 99, 25 recurrence* | | | | | | | | |
| Age at diagnosis | Continuous | 1.03 (0.98-1.09) | 0.278 | 0.56 | — | — | | |
| Tumor stage | pT2a-c vs. pT3a-c | 4.05 (1.80-9.12) | 0.001 | 0.68 | — | — | | |

TABLE 7-continued 4-miRNA prognostic ratio model (Example 1 + 5). Prognostic potential of 4-miRNA ratio model [miR-10b-5p × miR-23a-3p)/(miR-133a-3p × miR-374b-5p] assessed by uni- and multivariate Cox regression analyses of biochemical recurrence-free survival in three RP cohorts.

| Variable | Characteristics | Univariate | | | Multivariate-Final[c] | | | |
|---|---|---|---|---|---|---|---|---|
| | | HR (95% CI) | P value | C-index[a] | HR (95% CI) | P value | C-index[b] | |
| Surgical margin status | Negative vs. positive | 3.81 (1.70-8.54) | 0.001 | 0.63 | 2.52 (1.06-6.00) | 0.037 | 0.73 | 0.78 |
| Preoperative PSA | Continuous | 1.09 (1.06-1.13) | <0.001 | 0.66 | 1.07 (1.03-1.12) | <0.001 | | |
| 4-miRNA ratio model | Continuous | 0.62 (0.42-0.91) | 0.014 | 0.59 | 0.75 (0.53-1.07) | 0.115 | | |

Abbreviations: CI, confidence Interval; HR, hazard ratio; PSA, prostate specific antigen; pT, pathological tumor stage; RP, radical prostatectomy.
[a]Predictive accuracy, estimated by the Harrell concordance index (C-index).
[b]Left column, C-index based on clinicopathological variables only (i.e. excluding 4-miRNA prognostic ratio model); right column, C-index based on all variables included in the model.
[c]The 4-miRNA prognostic ratio model was analyzed in multivariate analysis including tumor stage, Gleason score, surgical margin status, and preoperative PSA. In the final multivariate model, variables failing the global multivariate analysis were excluded by stepwise backward selection.
*Gleason score was excluded from analysis in cohort 3, because the low Gleason score group (5-6) had no events, causing error in the analysis.
Significant P values (P < 0.05) are marked in bold.

TABLE 8

2-miRNA prognostic ratio model (Example 1 + 6). Prognostic potential of 2-miRNA ratio model [miR-10b-5p/miR-374b-5p] assessed by uni- and multivariate Cox regression analyses of biochemical recurrence-free survival in three RP cohorts.

| Variable | Characteristics | Univariate | | | Multivariate-Final[c] | | | |
|---|---|---|---|---|---|---|---|---|
| | | HR (95% CI) | P value | C-index[a] | HR (95% CI) | P value | C-index[b] | |
| Cohort 1, n = 126, 56 recurrence | | | | | | | | |
| Age at diagnosis | Continuous | 1.00 (0.94-1.05) | 0.858 | 0.53 | — | — | | |
| Tumor stage | pT2a-c vs. pT3a-c | 3.12 (1.81-5.36) | <0.001 | 0.64 | — | — | | |
| Gleason score | 5-6 vs.7-10 | 2.73 (1.51-4.93) | 0.001 | 0.61 | 2.60 (1.41-4.79) | 0.002 | | |
| Surgical margin status | Negative vs. positive | 2.73 (1.59-4.70) | <0.001 | 0.63 | 3.20 (1.81-5.65) | <0.001 | 0.73 | 0.77 |
| Preoperative PSA | Continuous | 1.05 (1.02-1.08) | <0.001 | 0.62 | 1.04 (1.01-1.07) | 0.003 | | |
| 2-miRNA ratio model | Continuous | 0.73 (0.61-0.88) | 0.001 | 0.65 | 0.73 (0.62-0.87) | <0.001 | | |
| Cohort 2, n = 110, 49 recurrence | | | | | | | | |
| Age at diagnosis | Continuous | 0.97 (0.93-1.03) | 0.319 | 0.53 | — | — | | |
| Tumor stage | pT2a-c vs. pT3a-c | 3.00 (1.69-5.30) | <0.001 | 0.63 | — | — | | |
| Gleason score | 5-6 vs. 7-10 | 2.42 (1.23-4.73) | 0.010 | 0.59 | — | — | | |
| Surgical margin status | Negative vs. positive | 3.37 (1.89-6.00) | <0.001 | 0.64 | 3.20 (1.76-5.84) | <0.001 | 0.73 | 0.74 |
| Preoperative PSA | Continuous | 1.05 (1.03-1.07) | <0.001 | 0.72 | 1.05 (1.03-1.07) | <0.001 | | |
| 2-miRNA ratio model | Continuous | 0.80 (0.64-1.00) | 0.047 | 0.54 | 0.79 (0.62-1.00) | 0.047 | | |
| Cohort 3, n = 99, 25 recurrence* | | | | | | | | |
| Age at diagnosis | Continuous | 1.03 (0.98-1.09) | 0.278 | 0.56 | — | — | | |
| Tumor stage | pT2a-c vs. pT3a-c | 4.05 (1.80-9.12) | 0.001 | 0.68 | — | — | | |
| Surgical margin status | Negative vs. positive | 3.81 (1.70-8.54) | 0.001 | 0.63 | 3.46 (1.43-8.35) | 0.006 | 0.73 | 0.79 |
| Preoperative PSA | Continuous | 1.09 (1.06-1.13) | <0.001 | 0.66 | 1.07 (1.03-1.11) | <0.001 | | |
| 2-miRNA ratio model | Continuous | 0.44 (0.22-0.89) | 0.023 | 0.58 | 0.38 (0.18-0.83) | 0.015 | | |

Abbreviations: CI, confidence Interval; HR, hazard ratio; PSA, prostate specific antigen; pT, pathological tumor stage; RP, radical prostatectomy.
[a]Predictive accuracy estimated by the Harrell concordance index (C-index).
[b]Left column, C-index based on clinicopathological variables only (i.e. excluding miRNA ratio model); right column, C-index based on all variables included in the model.
[c]The 2-miRNA prognostic ratio model was analyzed in multivariate analysis including tumor stage, Gleason score, surgical margin, and preoperative PSA. In the final multivariate model, variables failing the global multivariate analysis were excluded by stepwise backward selection.
*Gleason score was excluded from analysis in cohort 3, because the low Gleason score group (5-6) had no events, causing error in the analysis.
Significant P values (P < 0.05) are marked in bold.

TABLE 9

| All miRs in miRBase ver 21 nomenclature | Seq ID No | Sequence |
|---|---|---|
| miR-106a-5p | 1 | AAAAGUGCUUACAGUGCAGGUAG |
| miR-10b-5p | 2 | UACCCUGUAGAACCGAAUUUGUG |
| miR-133a-3p | 3 | UUUGGUCCCCUUCAACCAGCUG |
| miR-152-3p | 4 | UCAGUGCAUGACAGAACUUGG |
| miR-185-5p | 5 | UGGAGAGAAAGGCAGUUCCUGA |
| miR-193a-5p | 6 | UGGGUCUUUGCGGGCGAGAUGA |
| miR-221-3p | 7 | AGCUACAUUGUCUGCUGGGUUUC |

TABLE 9-continued

| All miRs in miRBase ver 21 nomenclature | Seq ID No | Sequence |
|---|---|---|
| miR-23a-3p | 8 | AUCACAUUGCCAGGGAUUUCC |
| miR-30d-3p | 9 | CUUUCAGUCAGAUGUUUGCUGC |
| miR-326 | 10 | CCUCUGGGCCCUUCCUCCAG |
| miR-374b-5p | 11 | AUAUAAUACAACCUGCUAAGUG |
| miR-615-3p | 12 | UCCGAGCCUGGGUCUCCCUCUU |
| miR-625-3p | 13 | GACUAUAGAACUUUCCCCCUCA |
| miR-151a-5p | 14 | UCGAGGAGCUCACAGUCUAGU |

TABLE 10

61 miRNAs detected in all samples.

| miR name | miR name | miR name |
|---|---|---|
| hsa-let-7a-5p | hsa-miR-15a-5p | hsa-miR-29c-3p |
| hsa-let-7b-5p | hsa-miR-16-5p | hsa-miR-30b-5p |
| hsa-let-7c | hsa-miR-186-5p | hsa-miR-30c-5p |
| hsa-let-7f-5p | hsa-miR-191-5p | hsa-miR-30e-5p |
| hsa-let-7g-5p | hsa-miR-193b-3p | hsa-miR-320a |
| hsa-let-7i-5p | hsa-miR-1972 | hsa-miR-320b |
| hsa-miR-103a-3p | hsa-miR-197-3p | hsa-miR-328 |
| hsa-miR-106a-5p | hsa-miR-199a-3p | hsa-miR-342-3p |
| hsa-miR-107 | hsa-miR-19b-3p | hsa-miR-34a-5p |
| hsa-miR-10b-5p | hsa-miR-21-5p | hsa-miR-361-5p |
| hsa-miR-125a-5p | hsa-miR-221-3p | hsa-miR-365a-3p |
| hsa-miR-125b-5p | hsa-miR-22-3p | hsa-miR-423-3p |
| hsa-miR-1260a | hsa-miR-23a-3p | hsa-miR-423-5p |
| hsa-miR-126-3p | hsa-miR-23b-3p | hsa-miR-490-3p |
| hsa-miR-128 | hsa-miR-24-3p | hsa-miR-574-3p |
| hsa-miR-141-3p | hsa-miR-25-3p | hsa-miR-663a |
| hsa-miR-143-3p | hsa-miR-26a-5p | hsa-miR-664a-3p |
| hsa-miR-145-5p | hsa-miR-27b-3p | hsa-miR-92a-3p |
| hsa-miR-150-5p | hsa-miR-29a-3p | isa-miR-93-5p |
| hsa-miR-151a-5p | hsa-miR-29b-3p | hsa-miR-99a-5p |
|  |  | hsa-miR-99b-5p |

REFERENCES

1. Ferlay J, Soerjomataram I, Dikshit R, Eser S, Mathers C, Rebelo M, et al. Cancer incidence and mortality worldwide: Sources, methods and major patterns in GLOBOCAN 2012. International journal of cancer Journal international du cancer. 2014.
2. Carthew R W, Sontheimer E J. Origins and Mechanisms of microRNAs and siRNAs. Cell. 2009; 136:642-55.
3. Zeng Y, Cullen BR. Sequence requirements for micro RNA processing and function in human cells. RNA. 2003; 9:112-23.
4. Gregory R I, Chendrimada T P, Cooch N, Shiekhattar R. Human RISC couples microRNA biogenesis and post-transcriptional gene silencing. Cell. 2005; 123:631-40.
5. Kozomara A, Griffiths-Jones S. miRBase: annotating high confidence microRNAs using deep sequencing data. Nucleic Acids Res. 2014; 42:D68-73.
6. Friedman R C, Farh K K, Burge C B, Bartel D P. Most mammalian mRNAs are conserved targets of microRNAs. Genome research. 2009; 19:92-105.
7. Di Leva G, Garofalo M, Croce C M. MicroRNAs in cancer. Annual review of pathology. 2014; 9:287-314.
8. Bartels C L, Tsongalis G J. MicroRNAs: novel biomarkers for human cancer. Clin Chem. 2009; 55:623-31
9. Tong A W, Fulgham P, Jay C, Chen P, Khalil I, Liu S, et al. MicroRNA profile analysis of human prostate cancers. Cancer Gene Ther. 2009; 16:206-16
10. Andersen C L, Jensen J L, Orntoft T F. Normalization of real-time quantitative reverse transcription-PCR data: a model-based variance estimation approach to identify genes suited for normalization, applied to bladder and colon cancer data sets. Cancer Res. 2004; 64:5245-50
11. Benjamini Y, Hochberg Y. Controlling the False Discovery Rate: A Practical and Powerful Approach to Multiple Testing. Wiley: Journal of the Royal Statistical Society. Series B (Methodological), 1995.
12. Dramiński M, Rada-Iglesias, Enroth S, Wadelius C, Koronacki, et al. Monte Carlo feature selection for supervised classification (2008) Bioinformatics (2008) 24 (1): 110-117.
13. Dyrskjot L, Thykjaer T, Kruhoffer M, Jensen J L, Marcussen N, Hamilton-Dutoit S, et al. Identifying distinct classes of bladder carcinoma using microarrays. Nature genetics. 2003; 33:90-6.
14. Taylor B S, Schultz N, Hieronymus H, Gopalan A, Xiao Y, Carver B S, et al. Integrative genomic profiling of human prostate cancer. Cancer cell. 2010; 18:11-22.
15. Mestdagh P, Van Vlierberghe P, De Weer A, Muth D, Westermann F, Speleman F, et al. A novel and universal method for microRNA RT-qPCR data normalization. Genome biology. 2009; 10:R64.
16. Mestdagh et al. Nat Methods. 2014 August; 11(8):809-15.
17. Bustin, S. A. (ed.) A-Z of quantitative PCR, IUL Biotechnology Series 5 (2004) 882 pages.
18. Harrell (2001) Regression modelling strategies: with applications to linear models, logistic regression, and survival analysis. New York: Springer-Verlag.
19. Tom Mitchell, Tom. Machine Learning, McGraw Hill, 1997.
20. Hieronymus H, Schultz N, Gopalan A, Carver B S, Chang M T, Xiao Y, et al. Copy number alteration burden predicts prostate cancer relapse. Proc Natl Acad Sci USA. 2014; 111:11139-44.
21. Haldrup C, Mundbjerg K, Vestergaard E M, Lamy P, Wild P, Schulz W A, et al. DNA methylation signatures for prediction of biochemical recurrence after radical prostatectomy of clinically localized prostate cancer. J Clin Oncol. 2013; 31:3250-8.
22. Livak, K. J. and T. D. Schmittgen, Analysis of relative gene expression data using real-time quantitative PCR and the 2(-Delta Delta C(T)) Method. Methods, 2001. 25(4): p. 402-8.

The invention claimed is:

1. An in vitro method for assessing the prognosis of a prostate cancer patient, comprising measuring the expression level of miR-10b-5p and miR-374b-5p in a sample of prostate cells obtained from said patient, wherein a changed expression level of said miR-10b-5p and miR-374b-5p, as compared to a reference expression profile, is indicative of the prognosis of said patient, and treating said patient with a suitable therapy based on the prognosis of said patient.

2. The method according to claim 1, wherein expression levels are normalized expression levels.

3. The method according to claim 2, wherein expression levels are normalized to the expression level of miR-151a-5p.

4. The method according to claim 1, further comprising an assessment of increased probability that the prostate cancer will progress, comprising detecting the level of said miR-10b-5p and miR-374b-5p in a said sample and calculating a prognostic score (P) based on a dataset comprising the expression level data of said miR-10b-5p and miR-374b-5p.

5. The method according to claim 4, wherein the prognostic score (P) is calculated as the ratio of expression levels:

$$P = \frac{(\text{level of } miR23a-3p) \times (\text{level of } miR10b-5p)}{(\text{level of } miR133a-3p) \times (\text{level of } miR374b-5p)}.$$

6. The method according to claim 4, wherein the prognostic score (P) is calculated as the ratio of expression levels:

$$P = \frac{(\text{level of } miR10b-5p)}{(\text{level of } miR374b-5p)}.$$

7. The method of claim 1, wherein the expression level of said miR-10b-5p and miR-374b-5p is determined by the method of qRT-PCR.

8. The method of claim 1, wherein the expression levels of said miR-10b-5p and miR-374b-5p are measured by microarray.

9. The method of claim 1, wherein the RNA used to measure the expression level of said miR-10b-5p and miR-374b-5p is extracted from punch biopsies from regions of sections of FFPE blocks or snap-frozen tissue evaluated to comprise >90% tumor.

10. The method according to claim 1, wherein the 260/280 nm absorbance ratio of the RNA used to measure the expression level of said miR-10b-5p and miR-374b-5p is over 1.75.

11. A method of treating a patient in need of prostate cancer treatment, the method comprising: performing a test according to claim 1 to characterize the patient's prognosis, and selecting an appropriate therapy for the patient based on this information.

12. A method of treating a patient in need of prostate cancer treatment, the method comprising: performing a test according to claim 1 to determine if the patient belongs to a low or high risk group with respect to prognosis, and selecting an appropriate therapy for the patient based on this information.

13. The method according to claim 1, further comprising measuring the expression level of an miRs selected from the group consisting of miR-133a-3p, miR-106a-5p, miR-152-3p, miR-185-5p, miR-193a-5p, miR-221-3p, miR-23a-3p, miR-30d-3p, miR-326, miR-615-3p, and miR-625-3p.

14. The method according to claim 13, wherein the expression levels of miR-133a-3p and miR-23a-3p are measured.

* * * * *

SEQUENCE LISTING

<160> NUMBER OF SEQ ID NOS: 14

<210> SEQ ID NO 1
<211> LENGTH: 23
<212> TYPE: RNA

<213> ORGANISM: Homo sapiens

<400> SEQUENCE: 1
aaaagugcuu acagugcagg uag                                          23

<210> SEQ ID NO 2
<211> LENGTH: 23
<212> TYPE: RNA
<213> ORGANISM: Homo sapiens

<400> SEQUENCE: 2
uacccuguag aaccgaauuu gug                                          23

<210> SEQ ID NO 3
<211> LENGTH: 22
<212> TYPE: RNA
<213> ORGANISM: Homo sapiens

<400> SEQUENCE: 3
uuuggucccc uucaaccagc ug                                           22

<210> SEQ ID NO 4
<211> LENGTH: 21
<212> TYPE: RNA
<213> ORGANISM: Homo sapiens

<400> SEQUENCE: 4
ucagugcaug acagaacuug g                                            21

<210> SEQ ID NO 5
<211> LENGTH: 22
<212> TYPE: RNA
<213> ORGANISM: Homo sapiens

<400> SEQUENCE: 5
uggagagaaa ggcaguuccu ga                                           22

<210> SEQ ID NO 6
<211> LENGTH: 22
<212> TYPE: RNA
<213> ORGANISM: Homo sapiens

<400> SEQUENCE: 6
ugggucuuug cgggcgagau ga                                           22

<210> SEQ ID NO 7
<211> LENGTH: 23
<212> TYPE: RNA
<213> ORGANISM: Homo sapiens

<400> SEQUENCE: 7
agcuacauug ucugcugggu uuc                                          23

<210> SEQ ID NO 8
<211> LENGTH: 21
<212> TYPE: RNA
<213> ORGANISM: Homo sapiens

<400> SEQUENCE: 8
aucacauugc cagggauuuc c                                            21

<210> SEQ ID NO 9
<211> LENGTH: 22

```
<212> TYPE: RNA
<213> ORGANISM: Homo sapiens

<400> SEQUENCE: 9
cuuucaguca gauguuugcu gc                                              22

<210> SEQ ID NO 10
<211> LENGTH: 20
<212> TYPE: RNA
<213> ORGANISM: Homo sapiens

<400> SEQUENCE: 10
ccucugggcc cuuccuccag                                                 20

<210> SEQ ID NO 11
<211> LENGTH: 22
<212> TYPE: RNA
<213> ORGANISM: Homo sapiens

<400> SEQUENCE: 11
auauaauaca accugcuaag ug                                              22

<210> SEQ ID NO 12
<211> LENGTH: 22
<212> TYPE: RNA
<213> ORGANISM: Homo sapiens

<400> SEQUENCE: 12
uccgagccug ggucucccuc uu                                              22

<210> SEQ ID NO 13
<211> LENGTH: 22
<212> TYPE: RNA
<213> ORGANISM: Homo sapiens

<400> SEQUENCE: 13
gacuauagaa cuuucccccu ca                                              22

<210> SEQ ID NO 14
<211> LENGTH: 21
<212> TYPE: RNA
<213> ORGANISM: Homo sapiens

<400> SEQUENCE: 14
ucgaggagcu cacagucuag u                                               21
```